(12) United States Patent
Hermeking et al.

(10) Patent No.: US 6,335,156 B1
(45) Date of Patent: Jan. 1, 2002

(54) 14-3-3σ ARRESTS THE CELL CYCLE

(75) Inventors: Heiko Hermeking; Bert Vogelstein, both of Baltimore; Kenneth W. Kinzler, BelAir, all of MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/210,748

(22) Filed: Dec. 15, 1998

Related U.S. Application Data

(60) Provisional application No. 60/069,416, filed on Dec. 18, 1997.

(51) Int. Cl.⁷ ............................. C12Q 1/02; C12N 5/08
(52) U.S. Cl. ........................................... 435/4; 435/366
(58) Field of Search ................................ 435/6, 325, 4, 435/366

(56) References Cited

U.S. PATENT DOCUMENTS

| | | |
|---|---|---|
| 5,424,191 A | 6/1995 | Prasad et al. ................. 435/7.1 |
| 5,776,676 A | 7/1998 | Prasad et al. .................. 435/6 |

OTHER PUBLICATIONS

W. Wang et al. "Molecular evolution of the 14–3–3 protein family." Journal of Molecular Evolution (Oct. 1996) 43(4)384–98.

H. Leffers et al. "Molecular cloning and expression of the transformation sensitive epithelial marker stratifin. A member of a protein family that has been involved in the protein kinase C signalling pathway." Journal of Molecular Biology (Jun. 20, 1993) 231(4)982–98.

G.L. Prasad et al. "Complementary DNA cloning of a novel epithelial cell marker protein, HME1, that may be down-–regulated in neoplastic mammary cells." Cell Grwth and Differentiation (Aug. 1992) 3(8)507–13.

Aitkenl, "14–3–3 proteins on the MAP" TIBS vol. 20, 1995 pp. 95–97.

Heiko Hermeking et al. "14–3–3σ is a p83–Regulated Inhibitor of G2/M Progression" Molecular Cell, vol. 1, 1–20, Dec. 1997.

*Primary Examiner*—Robert A. Schwartzman
*Assistant Examiner*—Bronwen M. Loeb
(74) *Attorney, Agent, or Firm*—Banner & Witcoff

(57) ABSTRACT

Exposure of colorectal cancer (CRC) cells to ionizing radiation results in a growth arrest, with cells blocked in both the G1 and G2 phases of the cell cycle. The G1 block has been shown to be due to the p53-mediated induction of the cyclin-dependent kinase inhibitor p21$^{WAF1/CIP1/SDI1}$, but the basis for the G2 arrest is unknown. Through a quantitative analysis of gene expression patterns in CRC cell lines, we have discovered that 14-3-3σ is strongly induced by γ-irradiation and other DNA-damaging agents. The induction of 14-3-3σ is mediated by a p53-responsive element located 1.815 kb upstream of its transcription start site. Exogenous introduction of 14-3-3σ into cycling cells results in a G2 block similar to that observed following irradiation. These results document a molecular mechanism for G2/M control that is regulated in human cells by p53.

27 Claims, 12 Drawing Sheets

(3 of 12 Drawing Sheet(s) Filed in Color)

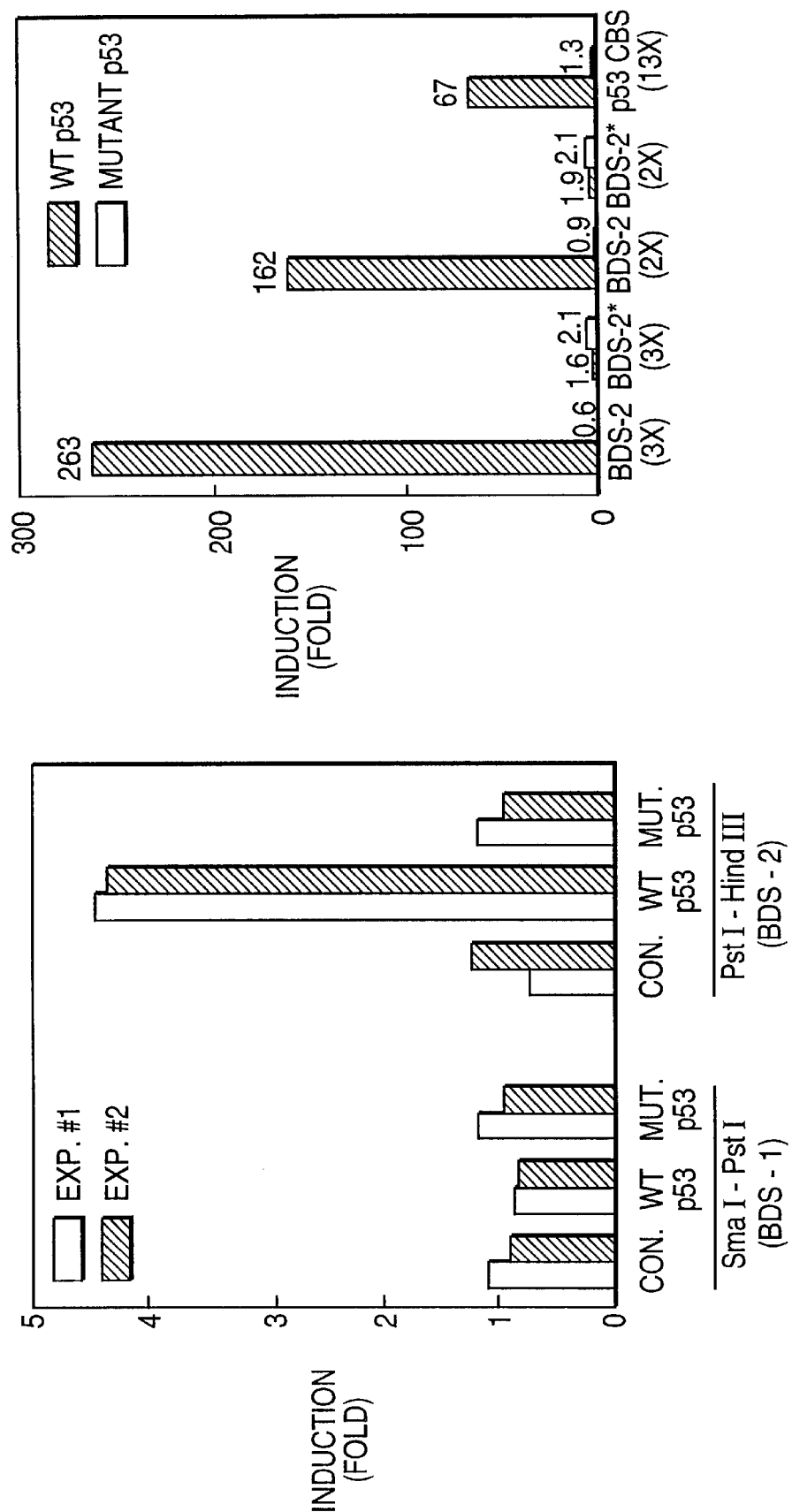

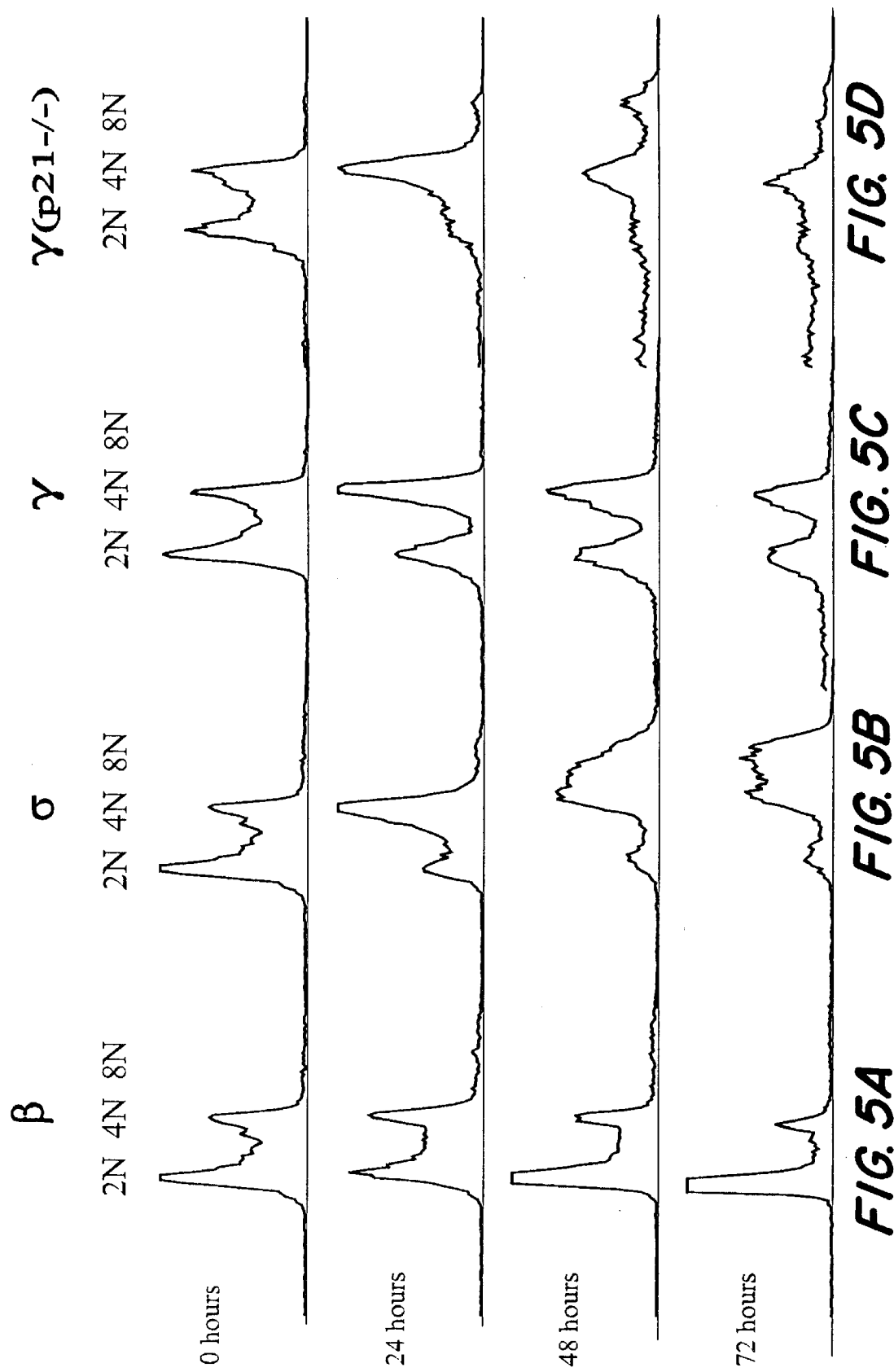

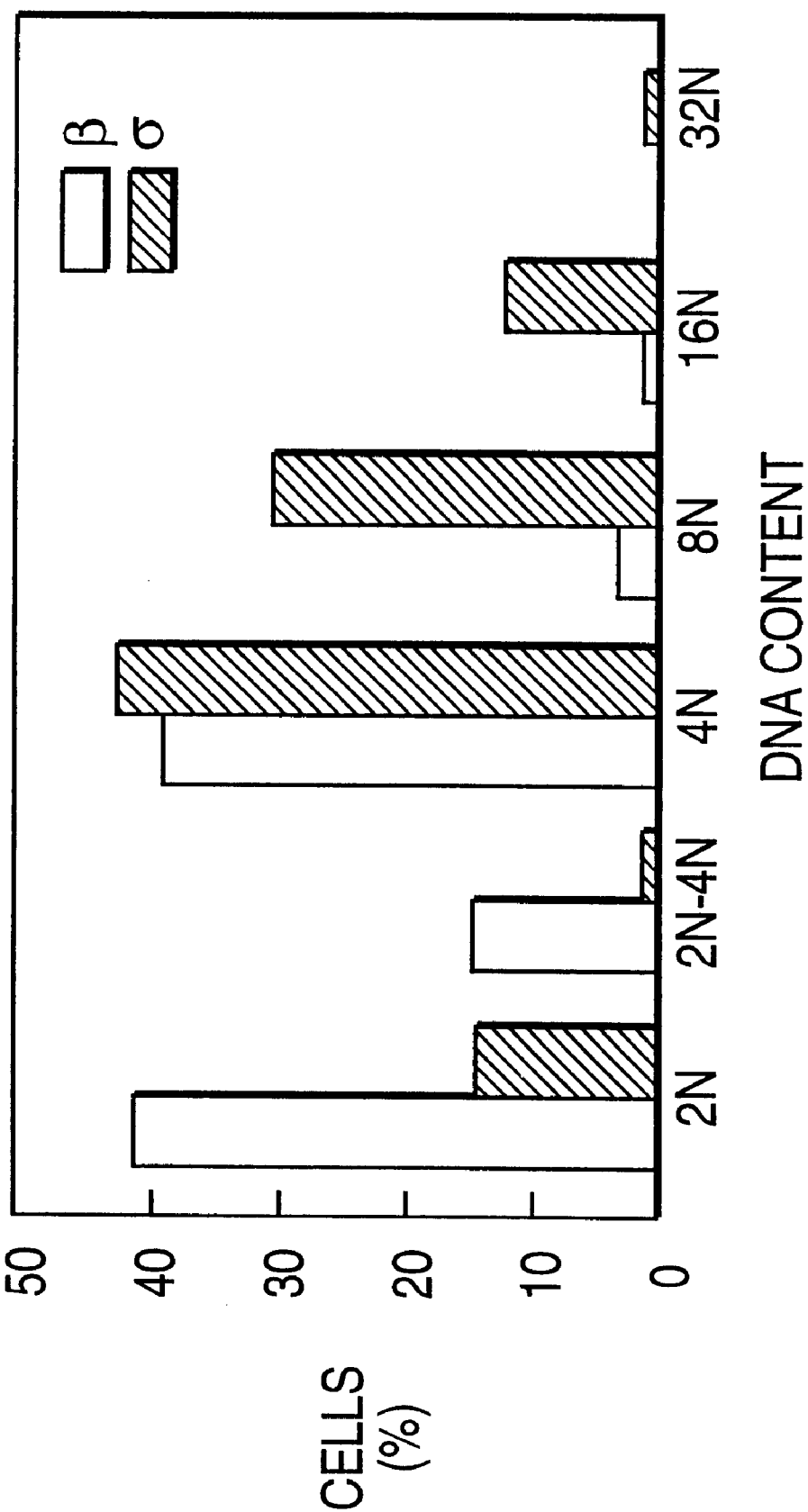

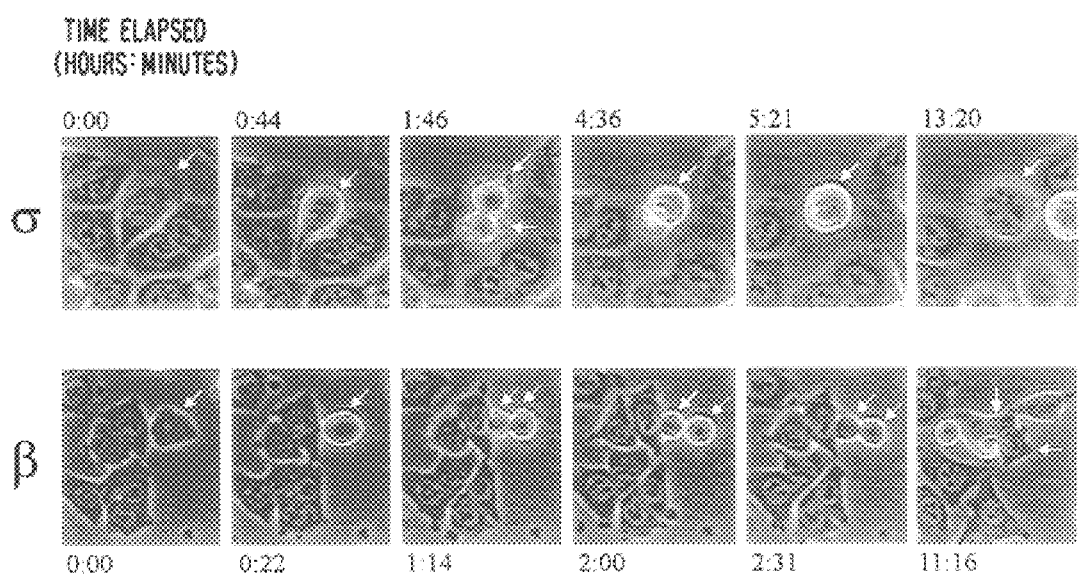

SEQUENCE LISTING

<160> NUMBER OF SEQ ID NOS: 18

<210> SEQ ID NO 1
<211> LENGTH: 1320
<212> TYPE: DNA
<213> ORGANISM: Homo sapiens

<400> SEQUENCE: 1

```
gagagacaca gagtccggca ttggtcccag gcagcagtta gcccgccgcc cgcctgtgtg      60
tccccagagc catggagaga gccagtctga tccagaaggc caagctggca gagcaggccg     120
aacgctatga ggacatggca gccttcatga aaggcgccgt ggagaagggc gaggagctct     180
cctgcgaaga gcgaaacctg ctctcagtag cctataagaa cgtggtgggc ggccagaggg     240
```

-continued

```
ctgcctggag gggtgctgtcc agtattgagc agaaaagcaa cgaggagggc tcggaggaga        300
aggggcccga ggtgcgtgag taccgggaga aggtggagac tgagctccag ggcgtgtgcg        360
acaccgtgct gggcctgctg acagccacc tcatcaagga ggccggggac gccgagagcc         420
gggtcttcta cctgaagatg aagggtgact actaccgcta cctggccgag gtggccaccg        480
gtgacgacaa gaagcgcatc attgactcag cccggtcagc ctaccaggag gccatggaca        540
tcagcaagaa ggagatgccg cccaccaacc ccatccgcct gggcctggcc ctgaactttt        600
ccgtcttcca ctacgagatc gccaacagcc ccgaggaggc catctctctg gccaagacca        660
ctttcgacga ggccatggct gatctgcaca ccctcagcga ggactcctac aaagacagca        720
ccctcatcat gcagctgctg cgagacaacc tgacactgtg gacggccgac aacgccgggg        780
aagaggggg cgaggctccc caggagcccc agagctgagt gttgcccgcc accgccccgc         840
cctgccccct ccagtccccc accctgccga gaggactagt atgggtgggg aggccccacc        900
cttctcccct aggcgctgtt cttgctccaa agggctccgt ggagagggac tggcagagct        960
gaggccacct ggggctgggg atcccactct tcttgcagct gttgagcgca cctaaccact       1020
ggtcatgccc ccacccctgc tctccgcacc cgcttcctcc cgaccccagg accaggctac       1080
ttctccccctc ctcttgcctc cctcctgccc ctgctgcctc tgatcgtagg aattgaggag      1140
tgtcccgcct tgtggctgag aactggacag tgcaggggc tggagatggg tgtgtgtgtg        1200
tgtgtgtgtg tgtgtgtgtg cgcgcgcgcc agtgcaagac cgagactgag ggaaagcatg       1260
tctgctgggt gtgaccatgt ttcctctcaa taaagttccc ctgtgacact caaaaaaaaa       1320
```

<210> SEQ ID NO 2
<211> LENGTH: 248
<212> TYPE: PRT
<213> ORGANISM: Homo sapiens

<400> SEQUENCE: 2

```
Met Glu Arg Ala Ser Leu Ile Gln Lys Ala Lys Leu Ala Glu Gln Ala
 1               5                  10                  15
Glu Arg Tyr Glu Asp Met Ala Ala Phe Met Lys Gly Ala Val Glu Lys
             20                  25                  30
Gly Glu Glu Leu Ser Cys Glu Glu Arg Asn Leu Leu Ser Val Ala Tyr
         35                  40                  45
Lys Asn Val Val Gly Gly Gln Arg Ala Ala Trp Arg Val Leu Ser Ser
     50                  55                  60
Ile Glu Gln Lys Ser Asn Glu Glu Gly Ser Glu Lys Gly Pro Glu
 65                  70                  75                  80
Val Arg Glu Tyr Arg Glu Lys Val Glu Thr Glu Leu Gln Gly Val Cys
                 85                  90                  95
Asp Thr Val Leu Gly Leu Leu Asp Ser His Leu Ile Lys Glu Ala Gly
            100                 105                 110
Asp Ala Glu Ser Arg Val Phe Tyr Leu Lys Met Lys Gly Asp Tyr Tyr
        115                 120                 125
Arg Tyr Leu Ala Glu Val Ala Thr Gly Asp Asp Lys Lys Arg Ile Ile
    130                 135                 140
Asp Ser Ala Arg Ser Ala Tyr Gln Glu Ala Met Asp Ile Ser Lys Lys
145                 150                 155                 160
Glu Met Pro Pro Thr Asn Pro Ile Arg Leu Gly Leu Ala Leu Asn Phe
                165                 170                 175
Ser Val Phe His Tyr Glu Ile Ala Asn Ser Pro Glu Glu Ala Ile Ser
            180                 185                 190
```

| Leu | Ala | Lys | Thr | Thr | Phe | Asp | Glu | Ala | Met | Ala | Asp | Leu | His | Thr | Leu |
|---|---|---|---|---|---|---|---|---|---|---|---|---|---|---|---|
| | 195 | | | | | 200 | | | | | 205 | | | | |

| Ser | Glu | Asp | Ser | Tyr | Lys | Asp | Ser | Thr | Leu | Ile | Met | Gln | Leu | Leu | Arg |
|---|---|---|---|---|---|---|---|---|---|---|---|---|---|---|---|
| | 210 | | | | | 215 | | | | | 220 | | | | |

| Asp | Asn | Leu | Thr | Leu | Trp | Thr | Ala | Asp | Asn | Ala | Gly | Glu | Glu | Gly | Gly |
|---|---|---|---|---|---|---|---|---|---|---|---|---|---|---|---|
| 225 | | | | | 230 | | | | | 235 | | | | | 240 |

| Glu | Ala | Pro | Gln | Glu | Pro | Gln | Ser |
|---|---|---|---|---|---|---|---|
| | | | | 245 | | | |

<210> SEQ ID NO 3
<211> LENGTH: 7680
<212> TYPE: DNA
<213> ORGANISM: Homo sapiens

<400> SEQUENCE: 3

```
ggatcccagc ctgcccctcc acttctctcc caagccaggt cccggcatgg gtgggttatg      60
ctcatgctgg caatacttga acgggtttta ttaatgctgg gtattttgca caattttata     120
gacctctttt ctacatagtc ttttttaaat ggaaggagaa aatgtcagcc acattactgt     180
ctgtgtagtg ccaggtgaag ggttatcaga aggctggttg gttttaataa gtttattcca     240
agagaccttc tggctggaat gagtgagagt gtgtgtgcat gtgtgtgtgt gttcatgtgt     300
gccctgtatg aatgtggctg ctcccagat ccctgggct gccccctgcc ccatcccctt     360
tgagtatcag aagcactctg agccaagggg acaggggca cgtgcactgg tcacgagaaa     420
accctgggct cccactgggg ctcagcccag cctcctatct ttccttcttc tatggacttc     480
agacagccag tgtctgggga ctctgccact ctaccccag ccctaccac cagccccag     540
gtgaggcttc cagctgggac ctgcccagac aggctgagc tgggcgtggt gggtggggtg     600
atggctctgg ggagcggctg ccatcctaca agccacaccc cctcctctga gctctgaata     660
tgggacccag tgccaggagc tggaagacaa ggtgtttctg ccaaacggga cctccatcca     720
gagaaaagga agaaggtgca gggtgggcca agaggcaagt gaaggttggc ctgagtctgg     780
gccggaaact cagaggatgt ttctcctctg ctgggagctg tagtttctta tcaaaataga     840
tattgttcca ccatcccct ccttggccct tcaagtgggc tgaagccttg gaaagtgaca     900
taggaagtcc ccagatcttg cccttctcac tccagaggct agtggtcaca gacagctggg     960
aatggcagcc acagagggtc cctctggaga aacagcttca ccccagcctc agggccctgg    1020
gcatcactgc agtggccctg ggaggtgagg aagaagctgg ctagaggagg gggctcccac    1080
ctacctttta tttaagccag tattctttgt tcctgcttgt aataaaactt cagttttataa    1140
gagttgcttt gctttggttt ggttttttgtt tgcttttcct ttgctgaggc cccaactggg    1200
agccctctgt tctttcagac aaatttggtt cttttcctggg gagactgtga aaggcaggc    1260
agcccagtga tctggctaca ttttccctca cctggctgga gctctgtccg ctggaggaag    1320
agcagagagg gctgcggctg agcccccatg ggcacgtgaa aagaggccat cctgtccct    1380
ctttgtcccc tccaccttcc cctgcctcag gggcttggag accccaaatt cttcttccct    1440
actgcctttc cactccgatc cccaatgagt gcccagctaa gaaaatgttt gagacagtag    1500
attccagttt gagagccgga gcttccctgg ctaccacctc caacctgggc caggggccc    1560
agccagacaa ctcataacac tggcccacct ctctggtatc tccctcagga ggacacctgt    1620
caggattttg ccatctcctg cacagcctga ggggagctaa caggcctctt tgcagagggt    1680
tagctggtaa gaccgtttct tccctgtcgg ccagcactgc ccgctcccct ccacacacca    1740
tctcatcctc atcgcatgcc tcgccaaccc catggagccc gtccatctgt ctggtgtgtg    1800
```

```
gtgcggtgtg tgtgctggtg gtggtagggt ctccagggac tccccgctaa gcagaaggat    1860
cgggatatag ggcaaggcta aaagcccagc cccattgtgg actgaggaag tacgttcgcg    1920
cagagcagct ctccagctgg aagaggaggt ggagggtgag gctggggaga ggatggcgaa    1980
cctgccctga ggtgcttggg tctgtgctgg tggggtcctg gtatgcaggg gccaccggtc    2040
actaacactc ttatgtcctg gctttctgtc ccgctgagc tttctctcac ccgcccgttt     2100
tctctcctgc ttcattgcct gctgcctaag ccttggccct tctctcgggc agaggcaggt    2160
gctgtggcag cacctctccc caccaccggg ccctgcagg ccgcctccct cctcccaggc     2220
ctgctaaccc tctctcttct ccttctttgc tgtcctgccg gggatctcca gtgtgtgcgg    2280
gggcttaagg acctcctgag gaccgctgct ctctgcctct ccaggaatgg cctgggggga    2340
gccaggcacc cggcacctcc acctgcctaa cctgtggccc atctgccacc atctgtgcct    2400
acagggtctg ccccccagcc tgcccggcct gtgtgctctc taggaccccca taggggcag   2460 gggctggcct ctttgcccca ttcccgctcc atgccggcca gagtgtagaa agccataacg    2520
cacgcagcca tcagcacaat aatgtgactc tacgctgata tgctcccctct ctcctccact   2580 gacttcccct tcccggattt gtgaggtgtc aagactagga atctggcctt agagcctgcc    2640
cctccacccc ctcagatcag gcatagccat agtcaagccc agcaggtttc ctcaggagct    2700
gtctggggtg ttgatggtgg atgacgctgc tgaacaagtt tggtgactgt tctaagcaca    2760
actggcttga tactgttccc acggcctgtc cacctcccac ccccaacccct ccaccagagt   2820 aggtaggatg tagggagggt gcgtgccgcc tttgctctag gcactgaggg accaagctag    2880
ccgtgcacag ccccatacac ttcaggggcg taaaggaaag agctgagcca aggaaaatca    2940
gctgagccca gggctggggg ctgcttgtct gctatcctgt acctttttt tttttaacca     3000 aaataaagat tcccctcttc ttgccatacc attggctgtc tggtggcgcc tttactttgg    3060
ggcccaggga tgggacctgc agtgggcgtg tggaacatat ggctccccct cgctcccagc    3120
tttcttccag ctggccagtg ctgctctgga gatttacaag cacaacgaag ccaggaggga    3180
cacaggaaaa gtggctgaca tccttttcac tctgcccctc cagaactctt ggtctcaatt    3240
ccagacacca cccagcctta gctgacctct ggattctgat aggtcccagt gcaggctgag    3300
acagagggtt taactccagt ttgggactgc atacccatg aactgagccc agcccagggt     3360
aacgatctca tggaaacttc tctctcccca gttgctgcac tacatcaaga tacacacatg    3420
tgcatacact gtactatggg ctaaaaaaat acgttcagc aagggcttgc                3480 cgagtcccgg gcccattttc tcatcttaac ctgtgaggag gatgatgtca gccttttac    3540 agatgaggga actgagactc aaggaagaaa caggagctgc ccaaggtcac ccagctggca    3600
aagcagcaaa tcccagatcg gaacctgatc tctgccccga gctctgagcc atctgcacta    3660
cccaaggaat gaatacagcg gtgggaggat gagatcttgg agaaacccta aaattagaga    3720
atgtcatagc cagtagaggg cttagagttg atctgggcca gcctccttgt tttactgatg    3780
gagaaattga agcccagagg caggaaggga cctgcccaag gccttataac agagctggga    3840
tgcagtccca cactctgacc tcattccatt ctctctccat aaattctgca ctgtctctag    3900
actggactgg tttagatgtg ggatactcta aacagcagtg ccttcaagag aaaaagaatc    3960
agaactacga atcacttaaa agtaatgtaa gctactctgg gcacactgcc tatggggtcg    4020
ccctgctcca caaggagcca caaaataat taaataatt taatatccct tcccaaaggt      4080
aaccagtaaa gtaagctctt ggctaggtaa ctggactctt gttcacaact agccagtggg    4140
aaaaggtgct agagcttcct ctggccacct gtttaatttg atcattccaa gacagaaaca    4200
```

```
tttcttagga agttctttct agaatctacc tggtgtccct cccactgcta tcagagccct   4260
gtcctctgtc ctcagtggag gtagagagca atggttgct gctttcttca tcacaaccct    4320
tcaaagccta ttattaccag ctaagaagga ttggttgact atgggccaga gcccctgagc   4380
ctgctggtag aatggatgct gtacaggagg gtggggaggt agcaggcaga atgaggaaag   4440
ccccttttgag ctgcaacccc agctcctgtc ctgctgactc agacagctga ctgtggagct  4500
ccatgccctg ccagggcctg ctgcctcctg cccgtctgag ctcctgaact tgggaaatgg   4560
aggcccagga gcaaagggag gtacctgaga caggaactga gtcaggatca acaggccaga   4620
gcgggcagga ggtatcaggc agcctggctc ccagatgcac ccctgagctc cagcagggga   4680
ggagtaggaa tgaaggggct tccttgccct tgctcatggc tatgcggagg gcgtgaacca   4740
ccaccaggtc ctctggctta agtggcggga agcaaatggt ccctccctgg actcaggctc   4800
caaagttcct gggcctgcct tccaggttcc cagtgtcctg ggatctccag ctttccccag   4860
gacttgggga agccccggct ggatgactag tacaaatgaa ggcccctgag gttccaggac   4920
ctgctgaggt cacaggaata tcctagatca agcttgtcca acccacggcc cacaggctgc   4980
atgtggccca gaatggcttt gaatgcagcc caacacaaat tagtaaactt tcttaaaaca   5040
ttatgagatt ttttgcaaa tttttttttt tttttagct catcagttat tggtagtgtt     5100
ggtatatttt atgtgtggcc caagacaatt cttccaatgt ggcccaggga agccaaaga    5160
ttggacacgc ctgtcctaga tggagaggaa ggaggcagtg ctgagcacat ctggccattc   5220
atccatctgg agagagaagg ctatgggcaa actgcttcct ctcccctgta gacacccagc   5280
tgggaaggtc tggccttttgg taagtcctgg cttggggtcc ttcctcattt cacagaacct   5340
aactctatgt tagtgctttg tgagtatatg ttgatcataa taagttgac gggatttttt     5400
cacatgataa taatagttgt catctggccg ggcatggtgg cttatgccta taatttcagc   5460
actttggaag gctgaggcag gtggatcact tgaggtcagc tgttcgagac cagcctggcc   5520
aacatggtga aaccacatct ctacttaaaa aaaaaaaaaa tacaaaaatt agctgggtgt    5580
ggtggtgcac cctgtaatc ccagctactc gggaggctga ggcaggagaa tcacttgaac    5640
ccaggaggtg gaggttgcag tgagctgaga ttgtgccact acactccagc ctgggtgaca   5700
agagcgaaac tccgtctcaa aaaaaagaa aataataata ataatagttg ccatccattc     5760
tactgtgctt tccattaact cgtgtaatcc tcacaagtcc cattttatag ttacaggaac   5820
tgaggctcac agagcttaaa tcacttggcc aaggccacaa acagctataa gaattacatt   5880
taggcagtct gattccaaag atactagtct attctgtatc tcatagacaa acaatacata   5940
ttcacttttt tgttgttgtt ttgttttgag acggagtctt gctctgtcac ccaggctgga   6000
gtgcagtggc gccatctcgg ctcactgcaa cgtccgcctc ccgggttcaa gcgattctcc   6060
tgcctcagcc tcccgagtag ctgggactac aggcatgtgc caccatgccc ggctaatttt   6120
ttgtattttt agtagagaca gggttttcct gggttagcca gaatggtctc gatctcctga   6180
ccttgtgatc cacccacctc agcctcccaa agtgctgaga tgacaggcgt gagccaccgc   6240
gtccgaccta tattcactat ttataaattg gagagaataa gaaaatcaaa agggccaggt   6300
gtagtgactc acacctgtaa tcccagcact ttgggaagcc aaggcaggag gattgcttga   6360
acccagaagt tcgagaccag cctgggcaac atggtgagac cctgtctcta caaaaaatac   6420
aaaaattagc tgggcgttgt ggtgagcacc ttattcttag gaagctgagg caggaggatc   6480
acctgaggcc aagaggttg agactgcagt gagctgtgat cataccactg tacttcagcc    6540
tggacatcag agtaagaccc tatctctaaa aaggaaattg agaagaaaga aaatcaaagg   6600
```

-continued

```
gaagcaaaat cactcactct cactacctca agatacoctc tagaagttgg tattttagtg    6660
tggttcctat tgttttctgt gtcagttctc tgatttgagc aaaatctttg ggacgtcaaa    6720
cttaaaatcc cctttacttc cttggaaacc ctgtagcatt agcccagaca tgtccctact    6780
cctccttgtg gcaaagagaa ggatctcgtc tttggtcccc agagttctgg cctaagcctc    6840
cctccaggag ggaagatgag tgttcagaca ctcagagtag ctgggggaga cacaggcctg    6900
tgaaattatc ctggctcaac tattaggtcg gcagaatccc agtgaaggga gccctacctc    6960
tgagccccat ctaagctttg gctatgggtg gggcagataa gcaggaatcc atccctatag    7020
gctcaatgcc aacacccctta ggtgaaactc ttgatgaaac ttgaggccag ggctccggca    7080
agcagggaaa gaacgttggc aacagaggtc tccatctctg aggactctgc cagggggtcag   7140 agatggggca atggtcaaaa ggaaggaaca ggccaggcac agtggctcat gcccataatc    7200
ccagcacttt gggaggctga gcaggagga tcgcttgagc ccaggagttt gagacctgcc     7260
tgggcaatgt agtgagatct gctctctatt taaaaaaaaa aaaaggaaa gaacaagtaa     7320 acttctgaga aacaggctgg gggaggcatc acgtagctgg aattgctgcc ccataaaaca    7380
gaatggtatg tgtcactgcc acctcccttt ctcagtcctc tctctcccca ggttgctagc    7440
gtccccctgg gggatcaaac tggactgctt cccagcctca gacagagagc agtctgagtc    7500
aggcaggaaa gtgggacagc cggggagctg gaccccaccc tctgtgagcc ccgctggtac    7560
ctgatggcat gtggcttgga gagggcaggt gacctggcgt ggagggccag agggtaaatc    7620
ctcaaacaag tggcaacagg ccaccaactt gaaagggaaa attgtgtagt gatgggaaat    7680
```

<210> SEQ ID NO 4
<211> LENGTH: 20
<212> TYPE: DNA
<213> ORGANISM: Homo sapiens

<400> SEQUENCE: 4
aggcatgtgc caccatgccc                    20

<210> SEQ ID NO 5
<211> LENGTH: 23
<212> TYPE: DNA
<213> ORGANISM: Homo sapiens

<400> SEQUENCE: 5
gtagcattag cccagacatg tcc                23

<210> SEQ ID NO 6
<211> LENGTH: 20
<212> TYPE: DNA
<213> ORGANISM: Homo sapiens

<400> SEQUENCE: 6
rrrcwwgyyy rrrcwwgyyy                    20

<210> SEQ ID NO 7
<211> LENGTH: 22
<212> TYPE: DNA
<213> ORGANISM: Artificial Sequence
<220> FEATURE:
<223> OTHER INFORMATION: PCR PRIMER

<400> SEQUENCE: 7
acaggggaac tttattgaga gg                 22

-continued

```
<210> SEQ ID NO 8
<211> LENGTH: 19
<212> TYPE: DNA
<213> ORGANISM: Artificial Sequence
<220> FEATURE:
<223> OTHER INFORMATION: PCR PRIMER

<400> SEQUENCE: 8
aagggctccg tggagaggg                                               19

<210> SEQ ID NO 9
<211> LENGTH: 20
<212> TYPE: DNA
<213> ORGANISM: Artificial Sequence
<220> FEATURE:
<223> OTHER INFORMATION: PCR PRIMER

<400> SEQUENCE: 9
gaaaactacc cctaaaagcc                                              20

<210> SEQ ID NO 10
<211> LENGTH: 20
<212> TYPE: DNA
<213> ORGANISM: Artificial Sequence
<220> FEATURE:
<223> OTHER INFORMATION: PCR PRIMER

<400> SEQUENCE: 10
gttgggtggc aggtattagg                                              20

<210> SEQ ID NO 11
<211> LENGTH: 20
<212> TYPE: DNA
<213> ORGANISM: Artificial Sequence
<220> FEATURE:
<223> OTHER INFORMATION: PCR PRIMER

<400> SEQUENCE: 11
gtgtgtcccc agagccatgg                                              20

<210> SEQ ID NO 12
<211> LENGTH: 20
<212> TYPE: DNA
<213> ORGANISM: Artificial Sequence
<220> FEATURE:
<223> OTHER INFORMATION: PCR PRIMER

<400> SEQUENCE: 12
accttctccc ggtactcacg                                              20

<210> SEQ ID NO 13
<211> LENGTH: 37
<212> TYPE: DNA
<213> ORGANISM: Artificial Sequence
<220> FEATURE:
<223> OTHER INFORMATION: PCR PRIMER

<400> SEQUENCE: 13
cctgtagcat tagcccagac atgtccctac tccgtac                           37

<210> SEQ ID NO 14
<211> LENGTH: 37
<212> TYPE: DNA
<213> ORGANISM: Artificial Sequence
<220> FEATURE:
<223> OTHER INFORMATION: PCR PRIMER
```

```
<400> SEQUENCE: 14
ggagtaggga catgtctggg ctaatgctac agggtac                              37

<210> SEQ ID NO 15
<211> LENGTH: 37
<212> TYPE: DNA
<213> ORGANISM: Artificial Sequence
<220> FEATURE:
<223> OTHER INFORMATION: PCR PRIMER

<400> SEQUENCE: 15
cctgtagaat tatcccagaa atttccctac tccgtac                              37

<210> SEQ ID NO 16
<211> LENGTH: 37
<212> TYPE: DNA
<213> ORGANISM: Artificial Sequence
<220> FEATURE:
<223> OTHER INFORMATION: PCR PRIMER

<400> SEQUENCE: 16
ggagtaggga aatttctggg ataattctac agggtac                              37

<210> SEQ ID NO 17
<211> LENGTH: 60
<212> TYPE: DNA
<213> ORGANISM: Artificial Sequence
<220> FEATURE:
<223> OTHER INFORMATION: PCR PRIMER

<400> SEQUENCE: 17
gcatgcggta cctaatacga ctcactatag ggcgaccacc atggagagag ccagtctgat     60

<210> SEQ ID NO 18
<211> LENGTH: 86
<212> TYPE: DNA
<213> ORGANISM: Artificial Sequence
<220> FEATURE:
<223> OTHER INFORMATION: PCR PRIMER

<400> SEQUENCE: 18
acctccggat ccttagctag cgtaatctgg aacatcgtaa gcgtaatctg gaacatcgta     60
tccaccgctc tggggctcct ggggag                                         86
```

14-3-3σ ARRESTS THE CELL CYCLE

This application claims the benefit of co-pending provisional application Serial No. 60/069,416, filed Dec. 18, 1997, which is incorporated by reference herein.

This invention was made with support from NIH grant CA 43460. The U.S. government therefore retains some rights in the invention.

TECHNICAL FIELD

The invention relates to the fields of diagnosis and therapy of cancers. More particularly, the invention relates to a protein which mediates cell cycle arrest upon damage to cellular DNA.

BACKGROUND OF THE INVENTION

It has long been known that DNA-damaging agents induce a cell cycle arrest, allowing time for repair and thus protecting the organism from the deleterious consequences of mutation. In mammalian cells, these arrests are often dependent on the functionality of the p53 gene product, a transcription factor which is translationally and post translationally activated following DNA damage (reviewed in Cox, Levine, and Morgan). Because p53 is mutated in a large fraction of cancers of diverse type, it is thought that the tumorigenic process may be intimately related to the disruption of p53-mediated control of the cell cycle. Accordingly, there has been much effort to define the molecular links between DNA damage, p53 expression, and cell cycle regulation.

Cells treated with ionizing radiation or other DNA-damaging agents arrest in both G1 and G2, with a consequent decrease in the fraction of cells in S phase. In colorectal cancer cells and many other epithelial cell types, 15–40% of the cells arrest in G1 and the remainder arrest in G2/M. The G1 block is in part mediated by $p21^{WAF1/CIP1/sDI1}$, a cyclin dependent kinase inhibitor, which is transcriptionally controlled by p53. Several studies have suggested that the G2/M block following DNA damage is also p53-dependent. However, the basis for this G2/M block, though accounting for the predominant form of arrest induced by radiation in many cell types, is unknown.

Thus, there is a need in the art for elucidation of the pathway by which p53 exerts its cell cycle arresting effects. There is also a need in the art for new diagnostic and therapeutic tools for evaluating and ameliorating human cancers.

SUMMARY OF THE INVENTION

It is an object of the invention to provide DNA molecules useful for diagnosing and treating human tumors.

It is another object of the invention to provide proteins useful for treating human tumors and for raising diagnostically useful antibodies.

It is yet another object of the invention to provide methods of suppressing growth of tumor cells.

It is an object of the invention to provide a method for screening potential therapeutic agents for treating cancer.

It is another object of the invention to provide methods for diagnosing cancer.

It is yet another object of the invention to provide a reporter construct, useful for screening potential antineoplastic agents.

It is an additional object of the invention to provide an antisense construct for inhibiting expression of a tumor suppressor gene.

It is still another object of the invention to provide antisense oligonucleotides for inhibiting expression of a tumor suppressor gene.

It is yet another object of the invention to provide methods for promoting growth of cells in which a tumor suppressor gene's expression is inhibited.

It is another object of the invention to provide a method for assessing susceptibility to cancers.

It is an object of the invention to provide a method for detecting the presence of wild-type p53 protein in a cell.

It is still another object of the invention to provide methods for identifying compounds which specifically bind to p53-specific DNA binding sequences which regulate σ expression.

It is an object of the invention to provide methods for screening for anti-cancer drugs.

It is another object of the invention to provide cell lines useful for screening for anti-cancer drugs.

These and other objects of the invention are provided by one or more of the embodiments described below. In one embodiment of the invention an isolated and purified sub-chromosomal DNA molecule is provided. The molecule encodes 14-3-3σ protein (σ) as shown in SEQ ID NO: 2. The sequence of cDNA encoding σ is shown in SEQ ID NO: 1.

In another embodiment of the invention an isolated and purified 14-3-3σ protein is provided. The protein has a sequence as shown in SEQ ID NO: 2.

In still another embodiment of the invention a method of suppressing growth of tumor cells is provided. The method comprises administration of a 14-3-3σ protein having a sequence as shown in SEQ ID NO: 2 to said cells.

In an additional embodiment of the invention a method of suppressing growth of tumor cells is provided. The method comprises administration to said cells of a DNA molecule which causes said cells to express 14-3-3σ, said DNA molecule having a sequence as shown in SEQ ID NO: 1.

According to another embodiment of the invention a method for screening potential therapeutic agents for the ability to suppress the growth of tumor cells by activating the expression of 14-3-3σ is provided. The method comprises incubation of a potential therapeutic agent with a cell which contains a 14-3-3σ reporter construct, said reporter construct comprising a 14-3-3σ transcription regulatory region covalently linked in a cis configuration to a gene encoding an assayable product. Further, the method comprises measurement of the production of the assayable product. A potential therapeutic agent is identified as useful if it increases the production by the cell of the assayable product.

In still another embodiment of the invention a method for diagnosing cancer is provided. The method comprises testing a tissue to determine if the tissue expresses less 14-3-3σ than normal tissue.

In another embodiment of the invention a method for diagnosing cancer is provided. The method comprises testing a tissue to determine if DNA in said tissue contains a mutant 14-3-3σ gene.

In still another embodiment of the invention a 14-3-3σ reporter construct is provided. The reporter construct comprises a 14-3-3σ transcription regulatory region covalently linked in a cis configuration to a gene encoding an assayable product.

In another embodiment of the invention an antisense 14-3-3σ construct is provided. The construct comprises: a transcriptional promoter; a transcriptional terminator; and a DNA segment comprising one or more segments of the 14-3-3σ gene, said gene segment located between said promoter and said terminator, said DNA segment being inverted with respect to said promoter and said terminator, whereby RNA produced by transcription of the DNA segment is complementary to a corresponding segment of 14-3-3σ RNA produced by human cells.

According to another embodiment a method of identifying a chromosome is provided. The method comprises the steps of contacting one or more chromosomes with a polynucleotide probe which comprises at least 11 contiguous nucleotides of the sequence shown in SEQ ID NO: 1; and detecting chromosomes which specifically bind to the polynucleotide probe, wherein a chromosome which specifically binds to the probe is identified as containing at least a portion of human chromosome 1.

In another embodiment of the invention a 14-3-3σ antisense oligonucleotide is provided. The oligonucleotide comprises at least ten nucleotides complementary to a sequence present in 14-3-3σ mRNA.

In yet another embodiment of the invention a triplex oligonucleotide is provided. The oligonucleotide comprises at least ten nucleotides complementary to a sequence present in a 14-3-3σ gene.

In still another embodiment of the invention a method is provided for promoting growth of cells. The method comprises: administering a 14-3-3σ antisense or triplex-forming oligonucleotide comprising at least ten nucleotides complementary to 14-3-3σ mRNA or 14-3-3σ gene, respectively, to said cells to inhibit the expression of 14-3-3σ. In an alternative method an antisense 14-3-3σ construct is administered to said cells to inhibit the expression of 14-3-3σ. The construct comprises:

a. a transcriptional promoter;
 b. a transcriptional terminator;
 c. a DNA segment comprising one or more segments of the 14-3-3σ gene, said gene segment located between said promoter and said terminator, said DNA segment being inverted with respect to said promoter and said terminator, whereby RNA produced by transcription of the DNA segment is complementary to a corresponding segment of 14-3-3σ RNA produced by human cells.

In still another embodiment of the invention a method is provided for assessing susceptibility to cancers. The method comprises testing a tissue selected from the group consisting of blood, chorionic villi, amniotic fluid, and a blastomere of a preimplantation embryo, to determine if DNA in said tissue contains a mutant 14-3-3σ gene.

In one embodiment a method is provided for detecting the presence of wild-type p53 protein in a cell, comprising the steps of: providing a cell lysate from a tissue of a human; incubating a DNA fragment comprising BDS-2 with the cell lysate to bind the DNA fragment to wild-type p53 present in the cell lysate; immunoprecipitating p53 protein to form a precipitate; determining the amount of the DNA fragment comprising BDS-2 present in the precipitate.

In another embodiment of the invention a method is provided for detecting the presence of wild-type p53 protein in a cell, comprising the steps of: providing a cell lysate from a tissue of a human; incubating the cell lysate with a DNA fragment comprising BDS-2 to bind the DNA fragment to wild-type p53 present in the cell lysate; removing all components of the cell lysate not bound to the DNA fragment; determining the amount of p53 bound to the DNA fragment.

In yet another embodiment of the invention a method is provided for identifying compounds which specifically bind to BDS-2 comprising the steps of: providing a test compound; incubating a DNA fragment comprising BDS-2 immobilized on a solid support with the test compound, to bind the test compound to the DNA fragment; determining the amount of test compound which is bound to the DNA fragment.

In even another embodiment of the invention a method is provided for identifying compounds which specifically bind to BDS-2 comprising the steps of: providing a test compound; incubating a BDS-2-containing DNA fragment immobilized on a solid support with the test compound and wild-type p53 protein to bind the wild-type p53 protein to the DNA fragment; determining the amount of wild-type p53 protein which is bound to the DNA fragment, inhibition of binding of wild-type p53 protein by the test compound suggesting binding of the test compound to the p53-specific DNA binding sequences.

In one embodiment of the invention, a method for screening test compounds to identify those which are potential anti-tumor agents is provided. The method comprises the steps of: determining DNA content of 14-3-3σ gene-defective human cells incubated in the presence and in the absence of a test compound, wherein a test compound which causes DNA accumulation in the 14-3-3σ gene-defective cell is identified as a potential anti-tumor agent.

In another embodiment of the invention, a different method of screening for potential anti-tumor agents is provided. The method comprises the steps of: determining viability or apoptosis of 14-3-3σ gene-defective human cells incubated in the presence and in the absence of a test compound; selecting a test compound which causes cell death or apoptosis in the 14-3-3σ gene-defective cell.

In yet another embodiment of the invention a homozygous 14-3-3σ gene-defective human cell line is provided.

In still another embodiment of the invention a pair of isogenic cell lines is provided. The first cell line is a homozygous 14-3-3σ gene-defective human cell line and the second cell line is a homozygous 14-3-3σ gene-normal human cell line.

According to another embodiment of the invention a method is provided for detecting p53 activity in a human tissue. The method comprises: contacting (a) a reporter construct comprising a 14-3-3σ transcription regulatory region covalently linked in a cis configuration to a gene encoding an assayable protein product, with (b) a cell lysate of a tissue of a human, under conditions suitable to transcribe RNA from the reporter construct and to translate the RNA to form protein; measuring production of the assayable product; wherein a cell lysate which increases the formation of assayable product identifies the tissue from which it was made as having wild-type p53.

In yet another embodiment of the invention a method is provided for detecting p53 activity in a cell. The method comprises: transfecting a test cell with a reporter construct comprising a 14-3-3σ transcription regulatory region covalently linked in a cis configuration to a gene encoding an assayable protein product; subjecting the test cell to a DNA damaging agent; measuring production of the assayable product in the test cell; comparing the production of the assayable product in the test cell subjected to a DNA damaging agent to production of the assayable product in a test cell which has not been subjected to the DNA damaging agent; wherein a test cell which produces more assayable product when subjected to the DNA damaging agent than the cell which has not been subjected to the DNA damaging agent is identified as having wild-type p53.

According to another aspect of the invention a method of detecting the presence of a wild-type p53 protein in a cell is provided. The method comprises the steps of: providing a histological section from a human; incubating the section with a detectably-labeled DNA fragment which comprises BDS-2 (SEQ ID NO: 5) to bind said DNA fragment to wild-type p53 present in the histological sample; removing unbound DNA fragment from the histological section; and determining the amount of DNA fragment which is bound to the histological sample.

In another aspect of the invention a method of identifying compounds which specifically bind to a p53-specific DNA binding sequence is provided. The method comprises the steps of: contacting a DNA fragment which comprises BDS-2 (SEQ ID NO: 5) with a test compound to bind the test compound to the DNA fragment; determining the amount of test compound which is bound to the DNA fragment.

Thus the subject invention provides the art with useful means for diagnosing and treating cancers in humans and other animals. Moreover, it opens new avenues for the design and screening of additional anti-neoplastic therapeutic agents which operate by means of a new mechanism as detailed below. Conversely, the subject invention provides a new approach for promoting the proliferation of cells when large numbers of such cells are desired.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1B) σ Expression following adriamycin treatment. Seven different CRC cell lines were treated with 0.2 ug/ml adriamycin (+) or vehicle (−) as indicated. RNA was prepared 24 hours following adriamycin treatment. Autoradiographs of Northern blots performed with σ, p21 and EF1 probes are shown. The p53 status of the respective cell lines is indicated on the top.

Figure 1A:
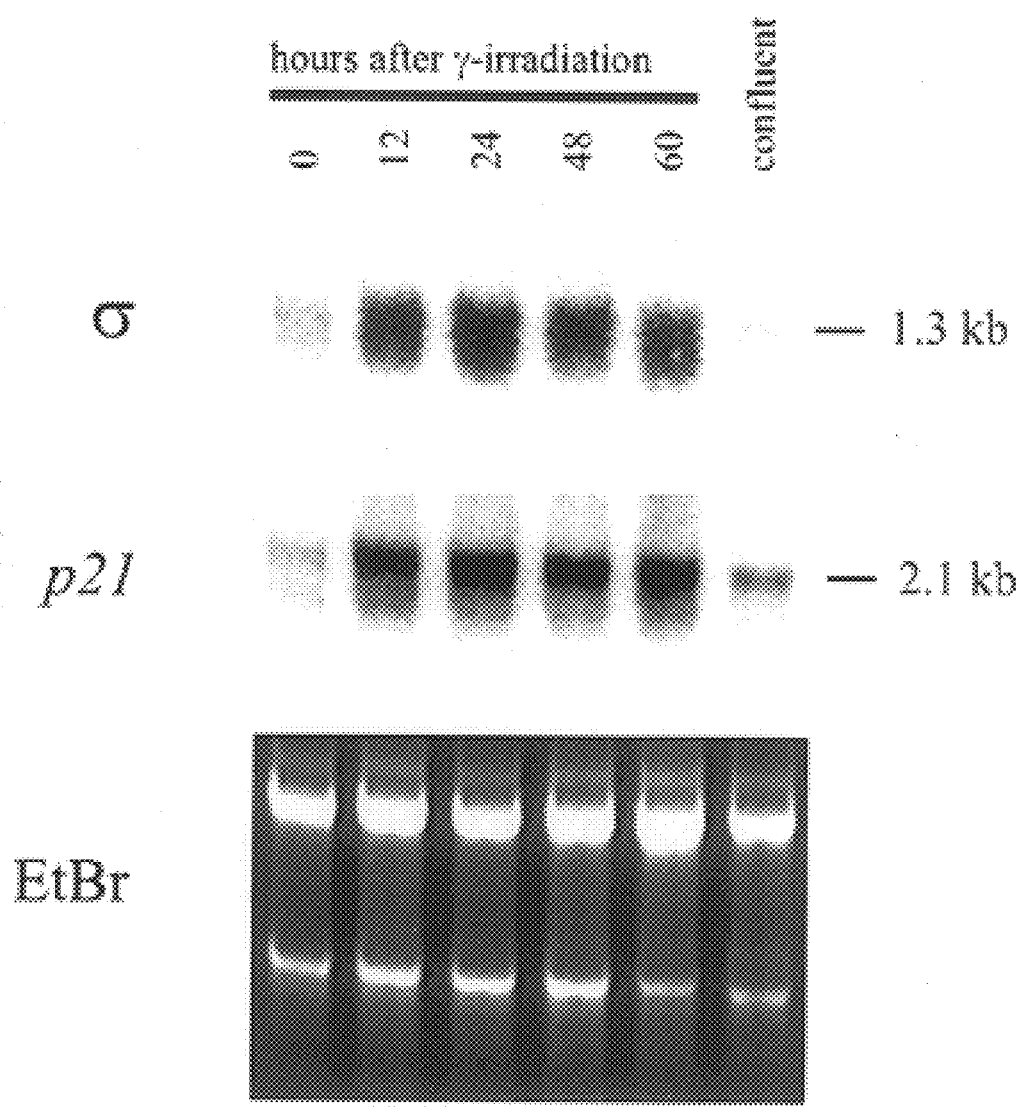
FIGS. 1A and 1B. σ Expression Following DNA Damage (FIG. 1A) σ Expression following irradiation. HCT 116 cells were γ-irradiated during exponential growth. RNA was prepared at the indicated times after irradiation or after reaching confluency in the absence of irradiation (confluent). Autoradiographs of Northern blots performed with σ and p21 probes are presented along with a picture of the ethidium bromide (EtBr) stained gel from which the blots were made. Sizes of the detected transcripts are indicated on the right.
Figure 1B:
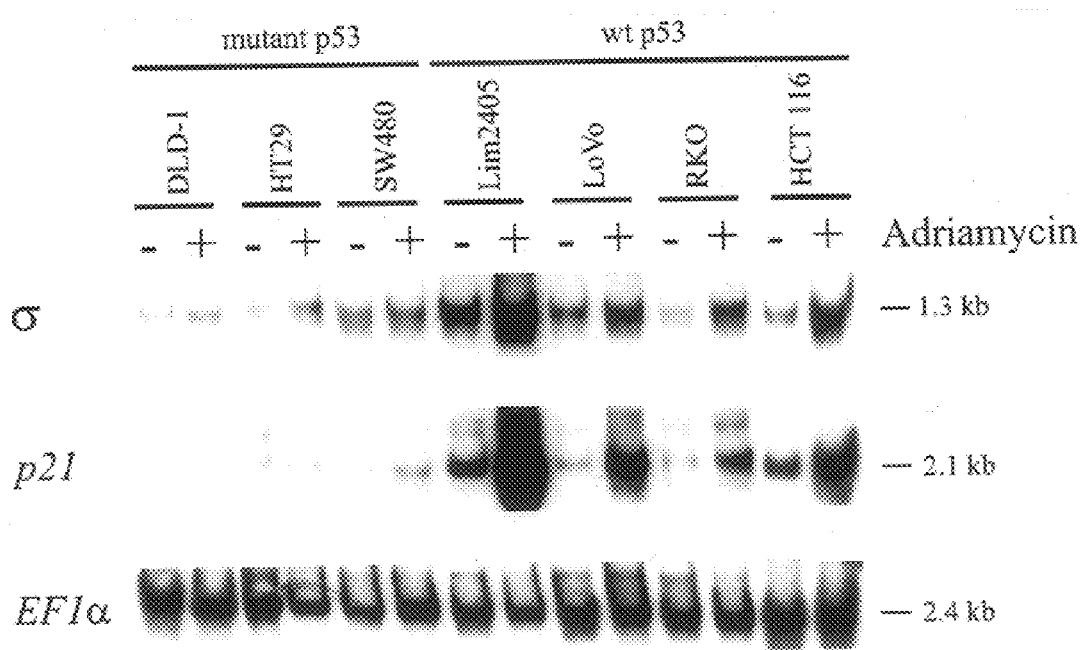
Figure 2A:
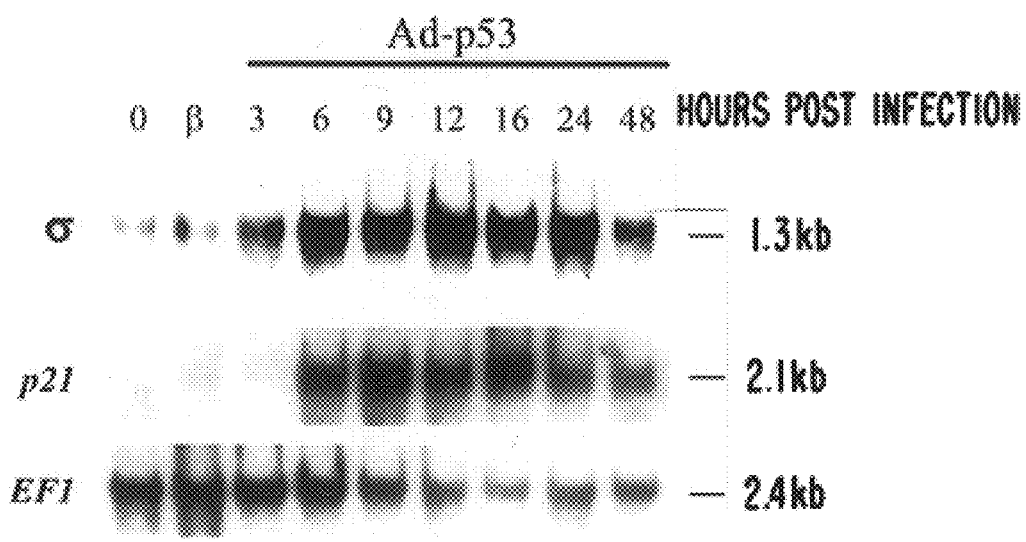
FIGS. 2A and 2B. σ Expression Following p53 Expression
Figure 2B:
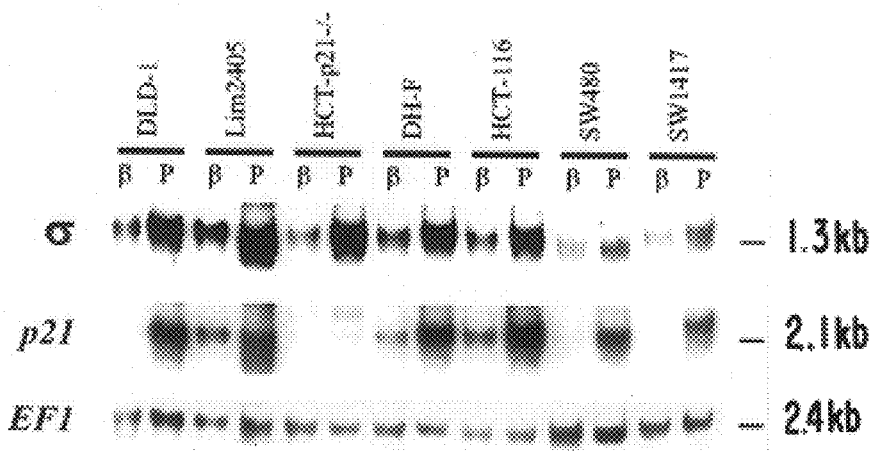

Cells were infected with Ad-p53 for the indicated time periods in (FIG. 2A) and with Ad-p53 (lanes marked P) or Ad-σ (lanes marked β in (FIG. 2B). Northern blotting was performed as in FIG. 1.

Figure 3A:
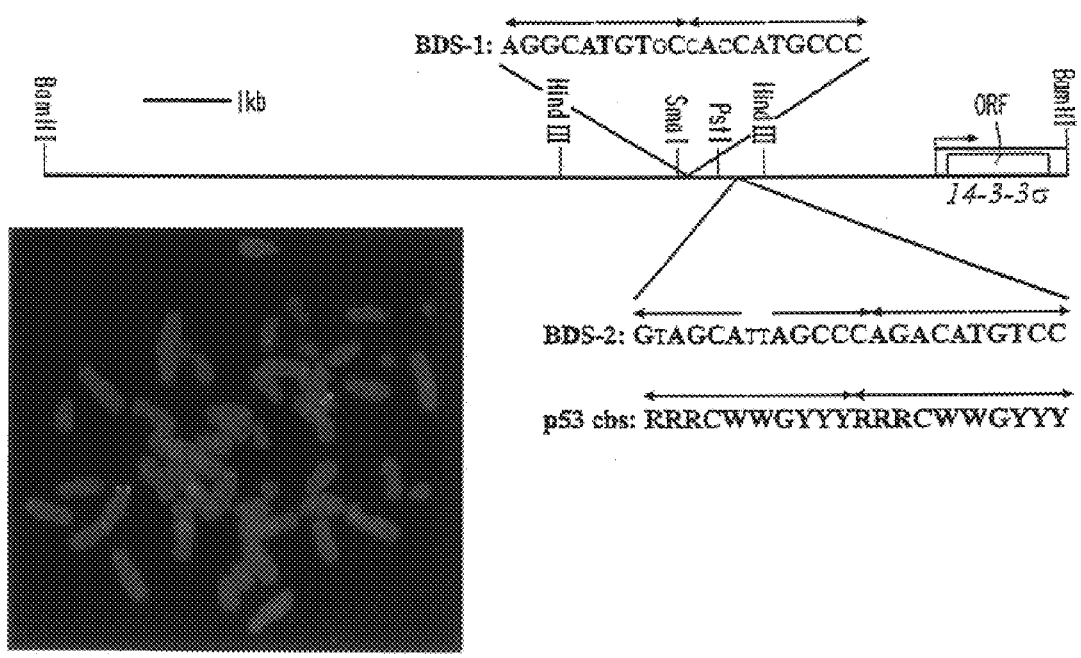

FIGS. 3A–3C. The σ Gene: Localization to 1p35, Genomic Organization and Identification of a p53 Binding Site (FIG. 3A) Genomic Structure and chromosomal localization of σ. A map of a 9.5 kb BamH I fragment of σ, indicating the potential p53 binding sites BDS-1 (SEQ ID NO: 4) and BDS-2 (SEQ ID NO: 5) identified by sequencing, is presented. The position of the σ open reading frame (ORF), the presumptive transcription start site (arrow), and selected restriction endonuclease sites used for vector constructions are indicated. The previously characterized p53-consensus binding site (cbs; E1 Deiry et al., 1992; SEQ ID NO: 6) is shown under the BDS-2 sequence (SEQ ID NO: 5), with R=purine, Y=pyrimidine, and W=A or T. The insert shows an example of FISH, localizing σ to 1p35.

(FIG. 3B) p53 responsiveness of σ promoter fragments. The indicated DNA fragments (BDS-1 and BDS-2) were cloned into a luciferase reporter vector containing a minimal promoter. SW480 cells were cotransfected with these reporters, a β-galactosidase encoding plasmid to control for transfection efficiency, and wild-type p53 (wt), mutant p53 (Mut.) or empty (Con.) expression constructs. Luciferase activity is expressed as a fold induction relative to the average obtained with the empty vector control.

(FIG. 3C) p53 responsiveness of the σ p53 binding site BDS-2. Reporters containing either two or three copies of the BDS-2 sequence were constructed as described in the examples. Four critical p53-binding residues of BDS-2 were altered in the reporter marked BDS-2*. These reporters were transfected and analyzed as in (FIG. 3B). The results are represented as fold induction by either wt p53 or mutant p53 compared to that resulting from transfections with an empty vector. Each bar represents the average of two independent experiments; the results in the two experiments varied by less than 20% of the average value indicated in the graph. The plasmid $PG_{13}$-luc, containing 13 copies of a consensus p53-binding site, was used as a positive control (Kern et al., 1992). The numbers in parentheses on the X-axis indicate the number of copies of the indicated p53-binding site in each reporter.

Figure 4A:
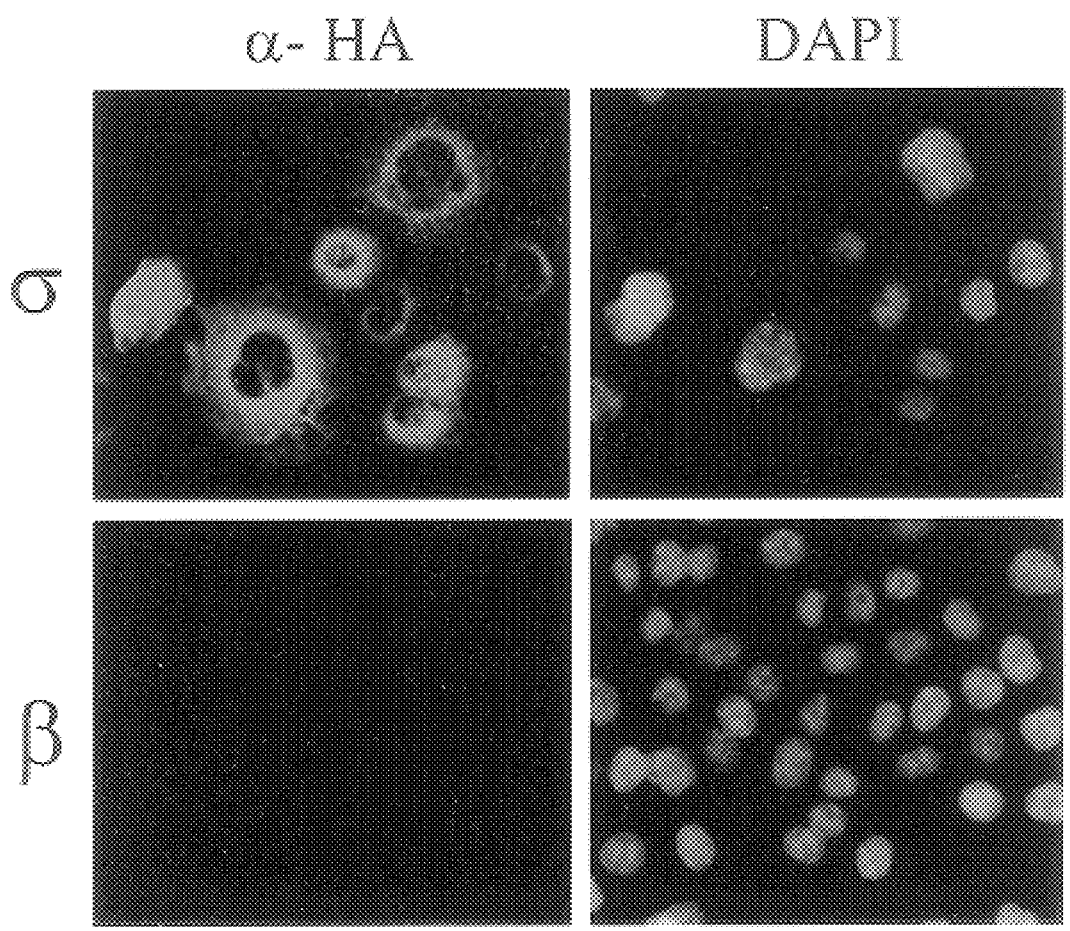

FIGS. 4A and B. Morphology of σ-expressing Cells (FIG. 4A) Immunohistochemical analysis of σ expressing cells. HCT116 cells were infected with Ad-σ or Ad-β for 30 h, then stained with an anti-HA antibody, recognizing the HA tag appended to the σ protein. Chromatin staining of the same cells with DAPI revealed the perinuclear localization of σ.

(FIG. 4B) Flow cytometric analysis of σ-expressing cells. The same cells and γ-irradiated HCT116 cells were fixed at the indicated times, analyzed by flow cytometry and assessed for forward light scatter to assess determine relative size. Each curve represents 10,000 cells.

FIGS. 5A through 5D. Exogenous Expression of σ Induces a G2 Arrest Followed by Polyploidy.

Subconfluent HCT116 cells were infected with Ad-β (FIG. 5A), Ad-σ (FIG. 5B), or treated with γ-irradiation (FIG. 5C). HCT116 cells made p21-deficient through homologous recombination (FIG. 5D) were similarly treated with γ-irradiation. The p21-deficient cells began to undergo apoptosis at the late time points. DNA content of at least 10,000 cells was analyzed by flow cytometry at the indicated times.

Figure 6A:
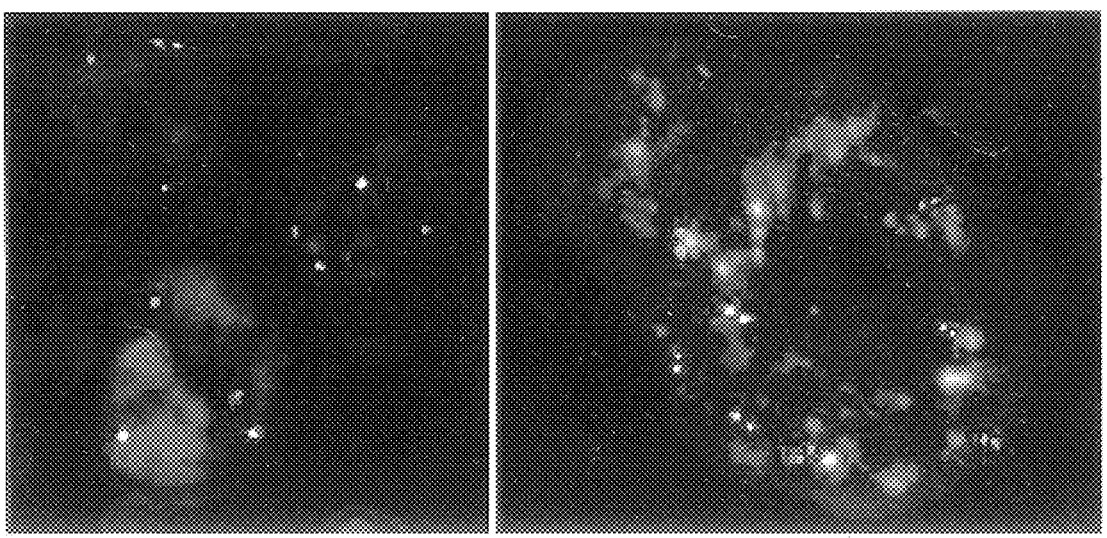

FIGS. 6A and 6B. FISH Analysis of σ-expressing Cells (FIG. 6A) Representative examples of HCT116 cells infected with Ad-β (left) or Ad-σ (right) and analyzed by interphase FISH. Hybridizations were performed with a chromosome 2p probe (red signals) and a chromosome 11q25 probe (green signals) 72 hours after infection. Note the paired signals in the σ-expressing cells. The Ad-β infected cell nuclei are apparently in G1, containing two unpaired signals per probe in each nucleus.

(FIG. 6B) Distribution of DNA content in σ expressing cells. The percentage of cells with the indicated DNA content per nucleus, as determined by FISH, is plotted. For Ad-β and Ad-σ infected cells, a total of 104 and 106 cells, respectively, were analyzed. '2N–4N' cells represent cells in which one doublet and one single signal were detected.

FIG. 7. σ Expression Prevents the Completion of Cytokinesis

HCT116 cells were infected with Ad-σ (top row) or Ad-β (bottom row) and observed with time-lapse video microscopy. Representative examples of single cells either performing an incomplete (Ad-σ) or a complete division (Ad-β) are shown (arrows). The times indicate the elapsed time since the first picture in the sequence was taken at approximately 31 hours after adenovirus infection.

Figure 8:
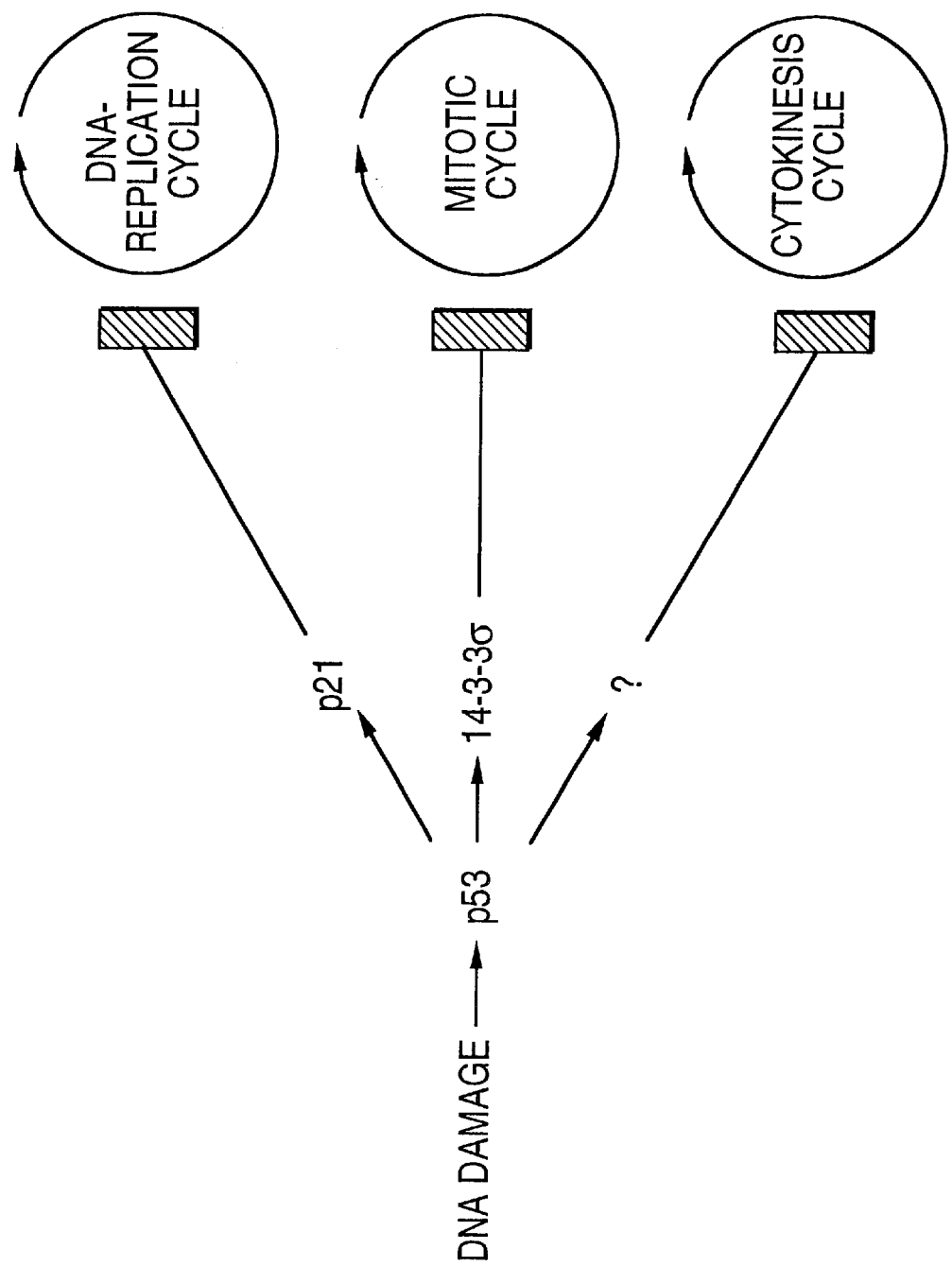

FIG. 8. Model for DNA Damage-induced Cell Cycle Regulation by p53

DNA damage activates the sequence-specific transcriptional capacity of p53 through translational and post-translational mechanisms (Cox, Levine, Morgan). The p53 protein then binds to the promoters of the p21 and σ genes, inducing their expression and resulting in a coordinated arrest in which cells are blocked in both G1 and G2 phases. The p21 gene product binds to and inhibits the cyclin-cdk complexes required for the transition from G1 to S phase (Harper and Elledge, 1996). The σ gene product is predicted to bind to and sequester phosphorylated Cdc25C, preventing Cdc25C from dephosphorylating Cdc2 and initiating the transition from G2 to M phase (Peng et al., 1997). In addition to activating p53, DNA damage results in other events required for blocking the cell cycle, including activation of Rad3 homologs (such as the ataxia talangiectasia gene ATM), which activates the Chk1 kinase that phosphorylates Cdc25c on $Ser^{216}$ (Furnari et al., 1997; Sanchez et al., 1997).

DETAILED DESCRIPTION OF THE PREFERRED EMBODIMENTS

We have analyzed the patterns of gene expression following irradiation of a human CRC cell line expressing wildtype (wt) p53. These cells arrested mostly in G2 and this arrest was accompanied by changes in gene expression. The most intriguing of the identified changes involved an increase in the expression of 14-3-3σ, a gene originally discovered through its expression in differentiating epithelial cells and a member of the 14-3-3 protein family. Numerous members of this family, including seven distinct human genes, have been identified, with diverse properties ascribed to them (for review see: Aitken; Wang). The function of 14-3-3σ (also called HME1 or stratifin and here referred to simply as "σ") has heretofore been unknown. We have discovered that σ expression in human cells is regulated by p53, and that exogenous expression of σ results in a G2 block similar to that observed following γ-irradiation.

DNA molecules according to the present invention are isolated and purified from other chromosomal genes. They may be either genomic sequences or cDNA sequences, i.e., they may or may not contain intervening sequences. A genomic clone of about 9.5 kb has been isolated which comprises the transcription regulatory region of the 14-3-3σ gene. The 14-3-3σ mRNA has been found to be approximately 1.3 kb.

Now provided with the correct sequence of 14-3-3σ cDNA (SEQ ID NO: 1), one of ordinary skill in the art can readily obtain the 14-3-3σ protein. It can be expressed in bacteria, yeast, or other convenient cell. Portions of it can be synthesized and linked to a carrier protein for immunization of laboratory animals to raise antibodies specifically immunoreactive with 14-3-3σ protein. The antibodies can be used to purify the 14-3-3σ protein from natural or recombinant sources. Such antibodies can be polyclonal or monoclonal, as is convenient for the particular application.

As described herein, 14-3-3σ protein has a growth-suppressing effect on tumor cells. Thus its administration to tumor cells may be desirable to effect such growth suppression. Other cells which are involved in proliferative diseases may also be targeted for 14-3-3σ-mediated growth suppression. Such proliferative diseases include psoriasis, polyps, warts, and inflammatory diseases. 14-3-3σ protein may be administered in suitable formulations to tumor cells. It may be microinjected, or simply supplied externally to tumor cells. It may be encapsulated, e.g., in liposomes. If 14-3-3σ-encoding DNA is administered to the tumor cells then the cells can express their own 14-3-3σ protein for growth suppression. Such DNA can be genomic or cDNA, as described above. Other cells involved in proliferative diseases may be treated similarly.

According to another aspect of the invention 14-3-3σ reporter constructs are provided. They are recombinant DNA molecules which contain a 14-3-3σ transcription regulatory region covalently linked in a cis configuration to a reporter gene. Many suitable reporter genes are known in the art, including, but not limited to β-galactosidase, luciferase, chloramphenicol acetyl transferase, neomycin phosphotransferase. If expression of the reporter gene is increased in the presence of a test compound, then one can assume that the test compound will function similarly to increase expression of 14-3-3σ when it is located downstream from its own transcription regulatory region, as it is in vivo. Since increased expression of 14-3-3σ is shown herein to have a growth suppressing effect on tumor cells, it can be assumed that the test compound which enhances the expression of the reporter construct will similarly have a growth suppressive effect in vivo. The transcription regulatory region of 14-3-3σ which is sensitive to the presence of wild-type p53 is located within about 1.815 kb of the 14-3-3σ transcriptional start site. The region includes the p53 binding site shown in SEQ ID NO:5. If the reporter construct is in a cell, the cell can be incubated with the test compounds and the effect on the expression of the reporter gene can be monitored and measured. Alternatively, the reporter construct may be employed in vitro in cell-free transcription and optionally translation systems.

14-3-3σ is shown herein to be regulated by wild-type but not mutant p53. Therefore, one can use the expression of 14-3-3σ as a marker for the expression of wild-type p53. Diminished 14-3-3σ expression, relative to normal tissues, can indicate cancer, just as diminished wild-type p53 expression or presence of mutated p53 expression can be indicative of cancer. Assays for 14-3-3σ expression can be used in addition to, or in place of, assays for wild-type p53 directly. Tissues which are suitable for comparison purposes to provide a normal control are typically adjacent, morphologically normal tissues. Tests for the presence or amount of 14-3-3σ expression can employ either antibodies specific for 14-3-3σ protein, nucleic acid probes of at least about 10 nucleotides complementary to all or a portion of the sequence of SEQ ID NO: 1, or other tests known in the art. Similarly, DNA of a tumor tissue can be tested to determine whether it contains mutations. 14-3-3σ mutations would be expected to confer a neoplastic phenotype on cells, as do p53 mutations. Mutations can be determined by determining the sequence of the genes or proteins in the tissue being tested, and comparing that sequence to that disclosed in SEQ ID NO: 1. Such mutations may arise in the germline or in somatic tissues. If the mutations arise in somatic tissues, then they will not be found in other tissues of the same individual. If the mutations arise in the germline, they will be found in all tissues of the body, and will, like germline p53 mutations, indicate a susceptibility to cancers. Tissues suitable for testing for germline mutations include blood, chorionic villi, amniotic fluid, and blastomeres if preimplantation fertilized embryos.

Antisense 14-3-3σ constructs contain a transcriptional promoter and a transcriptional terminator (polyadenylylation signal), with a DNA segment between them. The DNA segment comprises one or more segments of the 14-3-3σ gene, but that segment(s) is in an inverted orientation in the construct, compared to the orientation in the human genome. Transcription from the transcriptional promoter of the construct produces an (antisense) RNA molecule which is complementary to 14-3-3σ RNA which is produced from the 14-3-3σ promoter in normal human cells. The promoter used to make the antisense RNA molecule can be an inducible promoter which can be regulated by certain prescribed stimuli. For example, a metallothionein promoter or a hormone responsive promoter can be advantageously used. Other promoters and terminators can be used as is convenient in the particular application.

The antisense 14-3-3σ constructs of the present invention can be used in one type of cell to produce antisense RNA which is then applied to other cells by techniques known in the art. Alternatively, the 14-3-3σ constructs can be administered to the ultimate target cells in which regulation of 14-3-3σ is desired. Suitable means for introducing DNA constructs into cells are known in the art. Administration of antisense constructs may be by transfection, transformation, electroporation, fusion, etc., as is known in the art. Inhibition of 14-3-3σ expression causes cells to proliferate and prevents cell death. This can be particularly useful in situations where growing large numbers of certain cells in culture is desirable, such as in the case of culturing epidermal cells for transplantation. Alternatively, administration to certain cells of the body may be desirable, such as immune cells or cells of the gastrointestinal tract.

14-3-3σ antisense oligonucleotides are also provided for the same purpose as the antisense constructs, discussed above. The oligonucleotides are at least ten nucleotides and may be twenty or thirty nucleotides in length. They may consist of normal nucleotides or nucleotide analogs or mixtures of the two. Analogs include methylphosphonates, aminoalkylphosphonates, phosphorothioates, phosphorodithioates, substituted or unsubstituted phosphoramidates. The antisense oligonucleotides are typically linear, single-stranded molecules which are complementary to the natural 14-3-3σ mRNA made by human cells, though circular molecules can also be utilized. These can be administered to cells in liposomes, or naked, for uptake by the cells by passive or receptor-mediated transport. It is often desirable that the antisense oligonucleotide be designed to be complementary to the 5' end of the mRNA, in particular to the translation start site. However, other portions of mRNA molecules have been found to be amenable to antisense inhibition, and may be used in the practice of the present invention. It is also desirable to avoid portions of the mRNA as target for the antisense oligonucleotides which have secondary structures which involve hydrogen bonding with other portions of the molecule. For example, it is desirable to avoid regions which appear to be involved in formation of stems of stem-loop structures.

The expression of 14-3-3σ may also be inhibited by interference with transcription, by adding oligonucleotides or modified oligonucleotides than can form triple-stranded structures (triplexes) by complexing with a segment of the 14-3-3σ gene.

Based on the sequence information of BDS-2 (SEQ ID NO: 5), a number of diagnostic and therapeutic methods have been devised. According to one such method, cell lysates are tested for the presence or absence of wild-type p53 by virtue of its specific DNA binding ability. As it is known for various cancers and stages of cancers that one or both of the p53 alleles in tumor tissues can be mutant, testing for the presence or absence of wild-type p53 protein can provide diagnostic and prognostic information regarding a tumor and the patient. The cells to be tested are typically isolated from a tissue suspected of being neoplastic. Preferably the tissues are carefully prepared and isolated so that non-neoplastic tissues are not mixed with the neoplastic tissues, which can confound the analysis. Means for separating neoplastic tissues from non-neoplastic tissues are known in the art and include use of paraffin or cryostat sections, as well as flow cytometry. A cell lysate can be prepared from the tumor tissue according to any method known in the art. The cell lysate is then incubated with DNA fragments which comprise BDS-2 and bind the wild-type, activated p53 protein, under conditions which are conducive to such DNA/protein interactions. Alternatively, a histological sample can be analyzed by incubation with DNA fragments, as described for cell lysates. Wild-type p53 can be activated for DNA binding by irradiation of cells, treatment of cells with adriamycin, or other DNA-damaging agent, or by treating the p53 with monoclonal antibody pAB421.

It is known that p53 also binds non-specifically to DNA. Specific binding can be distinguished from non-specific binding by any means known in the art. For example, specific binding interactions are stronger than non-specific binding interactions. Thus the incubation mixture can be subjected to any agent or condition which destabilizes protein/DNA interactions such that the specific binding reaction is the predominant one detected. Alternatively, as taught more specifically below, a non-specific competitor, such as dI-dC, can be added to the incubation mixture. If the DNA containing the specific binding sites is labelled and the competitor is unlabeled, then the specific binding reactions will be the ones predominantly detected upon measuring labelled DNA.

According to one embodiment of the invention the DNA which is bound to p53 is separated from unbound DNA by immunoprecipitation with antibodies which are specific for p53. Applicants have found that use of two different monoclonal anti-p53 antibodies results in more complete immunoprecipitation than either one alone. Unbound DNA remains in suspension. The amount of DNA which is in the immunoprecipitate can be quantitated by any means known in the art. According to one aspect of the invention, the DNA fragment is labelled with a detectable moiety, such as a radioactive moiety, a colorimetric moiety or a fluorescent moiety. Techniques for so labelling DNA are well known in the art.

According to another embodiment of the invention, after incubation of p53 with specific binding DNA fragments all components of the cell lysate which do not bind to the DNA fragments are removed. This can be accomplished, among other ways, by employing DNA fragments which are attached to an insoluble polymeric support such as agarose, cellulose and the like. After binding, all non-binding components can be washed away, leaving p53 bound to the DNA/solid support. The p53 can be quantitated by any means known in the art. It can be determined using an immunological assay, such as an ELISA, RIA or Western blotting.

The diagnostic assay of the present invention has applicability not only with regard to cancers which are known to involve mutation of p53, but also with regard to human viruses such as human papilloma virus (HPV). HPV protein E6 binds tightly to wild-type but not mutant p53. See Wemess et al., Science, 248, 76–69 (1990). This tight binding is likely to block the interaction of p53 with its specific DNA binding sequences. By testing cells or cell extracts suspected of being infected with potentially tumor-inducing or hyperplasia-inducing strains of HPV or possibly other viruses, infected cells can be identified, because the E6 protein of the infected cells will have sequestered the wild-type p53, rendering it unable to bind to its specific DNA binding sequences. Such assays may be performed on cell extracts or on histological specimens.

Analogs of oligonucleotides may also be useful in the formation of complexes with double-stranded DNA. For example, certain modifications to the 3'-terminus can be employed to reduce the susceptibility of the oligonucleotide to nuclease degradation. Moieties which may be appended to the 3'- or 5'-termini include a substituted or unsubstituted amino group, polyethylene glycol, polylysine, acridine, dodecanol, and cholesterol. Oligonucleotides and analogs which may be used include methylphosphonates, phosphorothioates, phosphorodithioates, substituted or unsubstituted phosphoramidates, oligoribonucleotides, oligodeoxyribonucleotides, alpha-oligonucleotides and mixtures thereof. Other modifications to oligonucleotides may be desirable to increase the uptake by cells or nuclei of the oligonucleotides or to decrease nuclease sensitivity. All such modifications are within the contemplation of the invention.

Switchback linkers may also be incorporated into the midst of an oligonucleotide or analog. Such linkers are taught by Riordan and Martin (Nature, 350, 452, 1991). They are designed by molecular modeling to provide the proper spacing between portions of an oligonucleotide which are to interact with different strands of a double-stranded DNA molecule.

Single-stranded oligonucleotides or oligonucleotide analogs which are able to complex specifically with a p53-specific binding site as described above are also contemplated as part of the invention. Such oligonucleotides or analogs should comprise at least about ten nucleotides in length in order to have the requisite specificity with respect to the entire human genome. The oligonucleotides or analogs will comprise the BDS-1 or BDS-2 sequence (SEQ ID NO: 4 or 5) or the complement thereof. The oligonucleotides or analogs will preferably bind to the identified p53 binding regions. However, other binding regions in the human genome may well be found which are also suitable targets for the oligonucleotides or analogs of the present invention. These other binding sites may well be the primary targets of p53; complexation of these sites may inhibit the unregulated growth which characterizes neoplastic cells.

Double-stranded DNA fragments which comprise a BDS-2 sequence and are attached to an insoluble polymeric support are also contemplated by this invention. The support may be agarose, cellulose, polycarbonate, polystyrene and the like. Such supported fragments may be used in screens to identify compounds which bind to p53-specific DNA binding sites. Similarly, such supported fragments may be used to perform diagnostic tests on cell lysates from suspected tumor tissues. They may also be used in assays used to screen potential chemotherapeutic agents, as discussed infra.

Although any method can be employed which utilizes the BDS-2 p53-specific DNA binding site of the present invention, two particular methods are disclosed for screening for additional compounds to bind to p53-specific DNA binding sites. According to one method a test compound is incubated with a DNA fragment (optionally on a support), as described above. The amount of test compound which binds to the DNA fragment is determined. This determination can be performed according to any means which is convenient. For example, the amount of a compound which can be removed after incubation with the fragment can be compared to the amount originally applied. Alternatively, the test compound can be labelled and the amount which binds to the fragment can be assayed directly. In order to render this screening method more specific, soluble DNA fragments can be added to the incubation mixture. The soluble fragments do not have the ability to specifically bind to p53 wild-type protein.

According to another screening method for compounds to simulate or stimulate the specific DNA binding activity of p53, test compounds are incubated with supported DNA fragments as described above. However, in this method wild-type p53 protein is also added to the incubation mixture. The amount of p53 protein which binds to the DNA fragment is measured using methods as described above. The amount of p53 protein bound is compared to the amount which binds in the absence of the test compound. Any diminution of p53 binding which results from the presence of the test compound is presumptively due to the competition of the test compound with p53 for the specific DNA binding sites of the supported fragments. Direct binding of the test compound to the binding site fragments can be confirmed using the assay described above. Enhancement of p53 binding is presumptively due to acivation of p53 for DNA binding.

Mutant p53 genes or gene products can also be detected in body samples, such as, serum, stool, or other body fluids, such as urine and sputum. The same techniques discussed above for detection of mutant gene products in tissues can be applied to other body samples. By screening such body samples, a simple early diagnosis can be achieved for many types of cancers. In addition, the progress of chemotherapy or radiotherapy can be monitored more easily by testing such body samples for mutant p53 genes or gene products.

The methods of the present invention for diagnosis and therapy of neoplastic tissue is applicable across a broad range of tumors. These include lung, breast, brain, colorectal, bladder, mesenchyme, prostate, liver as well as stomach tumors. In addition the method may be used in leukemias and osteosarcomas. It thus appears that the p53 gene has a role in the development of a broad range of tumors. The methods of diagnosis and therapy of the present invention are applicable to any tumor in which p53 has a role in tumorigenesis. The diagnostic method of the present invention is useful for clinicians so that they can decide upon an appropriate course of treatment. For example, a tumor displaying loss of both p53 alleles suggests a more aggressive therapeutic regimen than a tumor displaying loss of only one p53 allele.

As a result of the discoveries of the present inventors, screening methods can be devised to isolate chemical agents which may have use in cancer therapy. Specifically, agents can be screened for the ability to affect the structure of mutant p53 molecules so that their ability to bind and/or transactivate at specific-DNA-binding sites is restored. The necessary components for such a screening method are provided by this invention and include DNA molecules which contain BDS-2 (SEQ ID NO: 5) and mutant p53 proteins which are found in tumors. Not all mutations in p53 destroy specific-DNA-binding ability. For example, mutations in phosphorylation sites of p53 have been made and tested; they retain binding activity. Such mutations have never been found in tumors. Mutations in p53 which are found in tumors are termed oncogenic herein.

One such prescreening method is an in vitro binding assay in which the strength of binding of a p53 mutant protein to a DNA molecule which comprises the BDS-2 binding site is measured. The strength of binding is also measured for a p53 mutant protein which has been incubated with a test substance. If incubation with the test substance increases the strength of binding, then the test substance is a candidate for use in anti-tumor therapy. Further testing will be desirable before use in humans is attempted.

Methods for measuring strength of binding can be any which are known in the art. See, for example, Tan and Richmond, Cell, vol. 62, pp. 367–377 (1990). One particular method employs immunoprecipitation. Briefly, purified p53 or a lysate of a cell expressing p53 is incubated with radiolabeled DNA and anti-p53 antibodies under conditions where proteins bind to DNA Protein A-Sepharose and poly-dIdC-poly-dIdC is then added for an additional incubation. A pellet is formed and washed and the proteins are removed by digestion with a protease and phenol extraction. The immunoprecipitated DNA is then analyzed by electrophoresis and quantified. Quantitation of the DNA can be by autoradiography, for example. The amount of DNA immunoprecipitated is proportional to the strength of binding of the p53 protein to the DNA, where the DNA is in excess.

According to another method, the ability of a mutant p53 protein from a tumor to transactivate transcription in vitro is assessed with and without a test substance. If the test substance increases the amount of transcription activated by the p53, then the test substance is a candidate for use in anti-tumor therapy. Transcriptional activation is measured using a transcription construct which comprises a reporter gene encoding a convenient assayable enzyme activity, such as chloramphenicol acetyltransferase or β-galactosidase, and a DNA segment comprising BDS-2. The BDS-2 binding site must be upstream, although the distance from the start of transcription is not critical. The binding site, which is adjacent to the reporter gene, may be from 0 to 10 kb upstream. In vitro transcription assay systems are well known in the art. See, for example, Lue, Science, vol. 246, 661–664 (1989).

According to still another method, transcriptional activation can be measured in vivo in a cell which has been cotransfected with a vector encoding a mutant p53 protein and a reporter gene construct comprising a gene encoding an assayable enzyme activity with a BDS-2 binding site adjacent and upstream therefrom. The transfected cells are treated with a test substance. If the amount of transactivation caused by the mutant p53 is enhanced by the test substance, then the substance is a candidate for anti-tumor therapy.

Transient expression constructs are conveniently made on plasmids and viral vectors, so that they can be propagated. These can also be used in vitro for transcription assays in the presence of RNA polymerase, ribonucleotides, and other cofactors.

A pair of isogenic cell lines is provided. The first cell line is a homozygous 14-3-3σ gene-defective human cell line and the second cell line is a homozygous 14-3-3σ gene-normal human cell line. These cell lines can be made as described in Waldman (1995). The cell lines are useful for screening compounds for their effects on the cell cycle, and potentially as anti-neoplastic compounds. Such cell lines when treated with a DNA damaging agent respond by accumulating DNA without undergoing mitosis, as well as entering the programmed cell death pathway. Thus detection of any of these events can be used to identify DNA damaging agents which are potentially useful as antineoplastics.

The BDS-2 region (SEQ ID NO: 5) has been found to be a very active and efficient region for p53-regulated transcription enhancement and binding. Thus the BDS-2 region can be used to detect p53 in human tissues and body samples. A reporter constuct can be made which has a 14-3-3σ transcription regulatory region covalently linked in a cis configuration to a reporter gene, i.e., a gene which encodes an assayable protein product. Preferably the regulatory region of σ is within 10 kb of the transcription initiation site for the reporter gene. The construct is used as a template for in vitro transcription and/or translation. Lysates of cells of a tissue of a human can be added and tested in the system to identify those which enhance transcription. Those lysates which enhance transcription are identified as containing wild-type, activated p53. Conditions suitable to transcribe RNA from the reporter construct and to translate the RNA to form proteins are well known in the art. Any means known in the art can be used to measure production of the assayable product. These can be enyzmatic reactions, immunological reactions, or whatever type of assay for a produced protein is convenient.

In a converse type of assay the reporter construct is transfected into cells to be tested. Production of the product of the reporter gene is measured. The transfected cell is then subjected to a DNA damaging agent, such as gamma-irradiation, or adriamycin. Again the production of the product is measured. A test cell which produces more assayable product when subjected to the DNA damaging agent than the cell which has not been subjected to the DNA damaging agent is identified as having wild-type, activated p53.

Wild-type activated p53 protein can also be detected using a histological type assay. A human histological section is incubated with a detectably-labeled DNA fragment which comprises BDS-2 (SEQ ID NO: 5) to bind said DNA fragment to wild-type p53 present in the histological sample. Unbound DNA fragment is removed from the histological section. The amount of DNA fragment which is bound to the histological sample can be determined, for example, by detection of readioactivity if the DNA fragment is labeled. Any method of quantitating DNA bound to a sample can be used.

Another use of BDS-2 is in the identification of useful compounds for anti-cancer chemotherapy. The strong interaction between BDS-2 and p53 makes BDS-2 an attractive target of drug screens. According to one method compounds are identified which specifically bind to BDS-2. A DNA fragment which comprises BDS-2 (SEQ ID NO: 5) is contacted with a test compound to bind the test compound to the DNA fragment. The amount of test compound which is bound to the DNA fragment is determined. A compound which specifically binds to BDS-2 is a candidate drug as a p53 mimetic. Further testing using other BDS-2 assays or other p53-mimetic assays can be used to confirm the utility of the compounds found.

According to the present invention, potential therapeutic agents are screened for the ability to cause DNA accumulation or cell death in 14-3-3σ gene-defective human cells. Preferably, agents are screened for the ability to preferentially cause DNA accumulation or cell death in 14-3-3σ gene-efective human cells as compared to 14-3-3σ gene-normal human cells. More preferably, agents are screened for the ability to cause DNA accumulation to at least four times the haploid DNA content of the 14-3-3σ gene-defective human cells.

Any means known in the art to generate a cell line which is defective in 14-3-3σ gene can be used to obtain the 14-3-3σ gene-defective cells. For example, a colonic cell line can be used to give rise to an isogenic σ-negative colonic cell line by promoterless homologous recombination. The disclosure of Waldman (1995) is expressly incorporated herein. A cell with two wild-type alleles of a 14-3-3σ gene is a 14-3-3σ gene-normal cell, for purposes of the present invention. Preferably, the 14-3-3σ gene-defective cell used in the assay is the same type of cell (organ source) as the 14-3-3σ gene-normal cell. More preferably the two cell lines are isogenic.

The DNA content of a cell incubated in the presence or absence of a test compound can be determined by any means known in the art. A DNA-binding dye may be employed to measure the DNA content. Procedures are available in the art to harvest cells, stain them with a DNA-binding dye, e.g., propidium iodide or H33258, and measure the incorporation of the DNA-binding dye by flow cytometry. Flow cytometry provides an ordinary artisan with information on the percentage of cells in a tested population with a diploid DNA content (2N), four times of haploid (4N), eight times of haploid (8N), etc. Alternatively, the DNA content of a cell can be determined by fluorescence in situ hybridization (FISH). Cells can be harvested, fixed on a slide, and hybridized with a chromosome probe. The DNA probe can be labeled and detected under fluorescence microscopy by any means known in the art. In one particular method, the DNA probe is biotinylated by nick translation and detected with fluorescein isothiocyanate (FITC) conjugated to avidin. The DNA content of a cell can be obtained by quantifying the intensity of the fluorescein signal through digital image acquisition and processing, which are readily available in the art.

It is well known in the art that viability of a cell can be determined by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. The most common dye used in the art for this purpose is trypan blue. Viability of cells can also be determined by detecting DNA synthesis. Cells can be cultured in cell medium with labeled nucleotides, e.g., $^3$H thymidine. The uptake or incorporation of the labeled nucleotides indicates DNA synthesis. In addition, colonies formed by cells cultured in medium indicate cell growth and is another way to test viability of the cells.

Apoptosis is a specific mode of cell death recognized by a characteristic pattern of morphological, biochemical, and molecular changes. Cells going through apoptosis appear shrunken, and rounded; they also can be observed to become detached from culture dish. The morphological changes involve a characteristic pattern of condensation of chromatin and cytoplasm which can be readily identified by microscopy. When stained with a DNA-binding dye, e.g., H33258, apoptotic cells display classic condensed and punctate nuclei instead of homogeneous and round nuclei.

A hallmark of apoptosis is endonucleolysis, a molecular change in which nuclear DNA is initially degraded at the linker sections of nucleosomes to give rise to fragments equivalent to single and multiple nucleosomes. When these DNA fragments are subjected to gel electrophoresis, they reveal a series of DNA bands which are positioned approximately equally distant from each other on the gel. The size difference between the two bands next to each other is about the length of one nucleosome, i.e., 120 base pairs. This characteristic display of the DNA bands is called a DNA ladder and it indicates apoptosis of the cell. Apoptotic cells can be identified by flow cytometric methods based on measurement of cellular DNA content, increased sensitivity of DNA to denaturation, or altered light scattering properties. These methods are well known in the art and are within the contemplation of the invention.

Abnormal DNA breaks are also characteristic of apoptosis and can be detected by any means known in the art. In one preferred embodiment, DNA breaks are labeled with biotinylated dUTP (b-dUTP). Cells are fixed and incubated in the presence of biotinylated dUTP with either exogenous terminal transferase (terminal DNA transferase assay; TdT assay) or DNA polymerase (nick translation assay; NT assay). The biotinylated dUTP is incorporated into the chromosome at the places where abnormal DNA breaks are repaired, and are detected with fluorescein conjugated to avidin under fluorescence microscopy.

Polynucleotides of the 14-3-3σ gene can be used to identify chromosomes and chromosomal segments. Particularly, they identify chromosome 1, segment p35. Any method for identifying chromosomes based on hybridization as is known in the art can be used with 14-3-3σ probes. For example, metaphase chromosome spreads can be contacted with a labeled 14-3-3σ probe and detected using FISH. This technique is described more fully below.

The experimental results described below demonstrate that γ-irradiation and other DNA damaging agents induce a substantial increase in the expression of σ in CRC cells. This induction is dependent on p53, as cells with an endogenous mutant p53 gene displayed no increase in σ expression. The molecular basis of the p53-dependence was shown to involve a single p53-binding site, located 1.8 kb upstream of the transcription start site. When exogenously expressed, σ caused a cellular phenotype remarkably similar to that observed following γ-irradiation, with an increase in cell size and an arrest in G2. These results strongly suggest that one of the molecular mechanisms underlying the G2 arrest following γ-irradiation is based on an activation of p53, which in turn transcriptionally activates σ. The combination of p21 and σ is likely to mediate a significant part of the cell cycle regulatory effects of p53 in epithelial cells following DNA damage (FIG. 8).

In *Schizosaccharomyces pombe*, the two σ homologs rad24 and rad25 function as checkpoints that ensure that DNA damage is repaired before mitosis is attempted. On the basis of the data presented above, we propose that σ functions similarly in human cells, arresting them in G2 and preventing mitosis after treatment with γ-irradiation or other DNA-damaging agents. Interestingly, deletion of rad24, and to a lesser extent rad25, led to premature entry into mitosis and a small cell size at division. This is exactly the counterpart of what occurred in human cells after overexpression of σ: there was a delay in mitotic entry associated with an increase in cell size.

The data reveal a conservation of mechanisms underlying cell cycle regulation following DNA damage. Moreover, results of others suggest a biochemical mechanism by which 14-3-3 homologs control this checkpoint. DNA damage results in the Rad3-dependent activation of Chk1 kinase, which subsequently phosphorylates the Cdc25C phosphatase on Ser$^{216}$ (Furnari et al., Sanchez et al.). The motif surrounding the phosphorylated Ser$^{216}$ represents a previously defined consensus binding site for 14-3-3 proteins (Muslin et al., 1996). The phosphorylated Cdc25C is thereby bound and sequestered by 14-3-3 and therefore unable to dephosphorylate Cdc2, a cyclin-dependent kinase required for entry into mitosis (Peng et al., 1997). Our data demonstrate that DNA damage not only results in phosphorylation of Cdc25C but also strongly induces expression of a 14-3-3 protein in colorectal cancer cells. Moreover, our results suggest that the 14-3-3 gene responsible for sequestering Cdc25C in colorectal cancer cells is likely to be 14-3-3σ. Interestingly, Cdc25C is also phosphorylated on $Ser^{216}$ in cycling cells in the absence of DNA damage. Overexpression of σ, as in the experiments reported here, would presumably bind and sequester the phosphorylated Cdc25 protein and prevent entry into mitosis in a similar manner as that observed following irradiation. The cytoplasmic localization of the exogenously introduced 14-3-3σ protein (FIG. 4A) suggests that 14-3-3 may prevent entry of Cdc25C into the nucleus. The p53-dependence of σ induction connects DNA damage and p53 with the cdk required for G2/M progression in much the same way as p21 connected p53 with the cdk's required for G1/S progression (FIG. 8).

The new data also provide an excellent example of the independence of the mitotic, cytokinetic, and DNA synthetic phases of the cell cycle (FIG. 8). Though the events that characterize these three phases have historically been viewed as sequential, it is becoming increasingly clear that they can proceed independently and that specific checkpoint genes link them in all eucaryotic cells. During a normal irradiation-induced cell cycle arrest, the three phases seem to be blocked by independent effectors. Among these effectors, p21 inhibits entry into S phase, σ prevents cells that have completed S phase from entering into mitosis, and cytokinesis is presumably inhibited by other, unidentified protein (s). The expression of these proteins following radiation thereby results in a coordinated arrest, in which cells are blocked in either G1 or G2 and can survive for prolonged periods. Experimental manipulation of these checkpoints results in an uncoordinated arrest. For example, σ overexpression in the absence of elevated p21 expression does not prevent chromatids from detaching from each other (FIG. 6A) or from re-initiation of S phase without an intervening mitosis (FIGS. 5, 6). Similarly, expression of σ in the absence of elevated levels of p21 prevents chromosome condensation and nuclear membrane breakdown, but does not prevent the onset of cytokinesis (which cannot be completed, presumably because the nucleus is still intact; FIG. 7). When such uncoordinated events are occurring in cells, the terms "G1" and "G2" are no longer applicable to describe their states.

Interestingly, though exogenous expression of σ resulted in the accumulation of cells containing a DNA content of 4N in all cells tested, additional rounds of DNA synthesis in the absence of mitosis ensued in HCT116 and some other colorectal cancer cells, but not in normal prostate epithelial cells. Eventually, these uncoordinated arrests resulted in the apoptotic death of the cancer cells. Such results have potentially important implications for cancer therapy. The p53 mutations that occur commonly in cancer abrogate part of the normal responses to DNA damage, i.e., induction of p21 and σ. In combination with other genetic alterations that may alter checkpoint monitoring or execution, the p53 mutations should result in an uncoordinated cell cycle, eventually resulting in the apoptotic death of the cancer cells.

Such differences in checkpoint function between normal and cancer cells may explain why current cancer chemotherapy is successful in some patients. Exploitation of these differences can lead to more specific chemotherapeutic agents.

EXAMPLE 1

This example demonstrates analysis of gene expression following γ-irradiation.

The human colorectal cancer cell line HCT116 expresses wild-type p53 and arrests following γ-irradiation in an apparently normal fashion, with ~25% of cells in G1 and ~75% of cells in G2 (see FIG. 5C). RNA was purified from HCT116 cells 60 hours following irradiation and analyzed by the SAGE (serial analysis of gene expression) technique. With SAGE, each RNA species is represented by a 15 base tag uniquely positioned near its 3' end. Tags are concatamerized and sequenced, and the abundance of each transcript determined from the relative number of tags. A library of 55,429 tags from γ-irradiated HCT116 cells was generated and found to represent 20,291 different mRNA's σ of which 6831 were represented by entries in GenBank, release 94). We initially focused on the 100 tags which appeared to be represented at higher levels in irradiated HCT116 cells compared to exponentially growing HCT116 cells (see Experimental Procedures).

Next, we determined whether any of these 100 tags were represented at significantly higher levels in a tag library from colon cancer cells expressing an exogenous p53 gene compared to the same cells in the absence of exogenous p53 (Polyak et al., 1997). Only three of the 100 tags were expressed at five-fold or higher levels in the p53-expressing cells. Database searching with the tag sequences tentatively identified one of the genes as that encoding σ and one as ISG, encoding a 15 kD protein induced by interferon; there were no matches for the third tag. The tag corresponding to σ was of particular interest in light of previous studies demonstrating that 14-3-3 homologs are essential for irradiation-induced G2 arrest in *Schizosaccharomyces pombe*. A total of six different 14-3-3 family members (σ, ξ, τ, β, η and PLA2) were represented in our SAGE libraries, but only σ was found to be expressed at higher levels following both irradiation and p53 expression.

Cells

Most cell lines used in this study were obtained from the American Type Culture Collection. The RKO and Lim2405 CRC cell lines were generous gifts from M. Brattain and R. Whitehead, respectively. The derivation of the HCT116 p21-/- (Waldman et al., 1995) and DH-F CRC cell lines have been described. CRC cells were cultured in McCoy's medium supplemented with 10% fetal bovine serum. Normal human fibroblasts, endothelial cells, and prostate epithelial cells and theri respective growth media were obtained from Clonetics. Irradiation was performed using a $^{137}Cs$ gamma irradiator at 1 Gy/minute for 12 minutes.

SAGE

SAGE was performed as previously described. In brief, polyadenylated RNA was converted to double-stranded cDNA with the inclusion of primer biotin-5'-$T_{18}$-3'. The cDNA was cleaved with Nla III and the 3'-terminal cDNA fragments were bound to streptavidin-coated magnetic beads (Dynal). After ligation of oligonucleotides containing recognition sites for BsmF I, tags were released from the beads by digestion with BsmF I. The released tags were ligated to one another. The resulting ditags were PCR amplified, isolated and concatemerized, and then cloned into the Sph I site of pZero (Invitrogen). Colonies were screened with PCR using M13 forward and M13 reverse primers. PCR products containing inserts of greater than 500 bp (>25 tags) were sequenced with the TaqFS DyePrimer kit and analyzed using a 377 ABI automated sequencer (Perkin Elmer) and the SAGE Software Package (Velculescu et al, 1995).

Candidate γ-irradiation induced genes were identified by comparing 55,429 tags from irradiated HCT116 cells to 5,266 tags isolated from exponentially growing, non-irradiated HCT116 cells. For a given number of evaluated tags, biasing the number so that more tags were derived from one library than the other allows a deeper analysis of the state wherein increased expression is expected. However, because this bias is more likely to produce false positives, any candidate tag will require independent validation of its induction. In the studies reported here, candidate irradiation-associated tags were firther evaluated by comparison to those represented in a library generated after ectopic p53 expression in CRC cells (Polyak et al., 1997), as described in the text.

EXAMPLE 2

This example demonstrates induction of σ by DNA damage.

Northern blotting with a radiolabeled probe generated from σ cDNA was performed to confirm the SAGE results. As shown in FIG. 1A, σ transcripts were induced within 12 hours of irradiation and remained elevated for at least 60 hours. Interestingly, no induction of σ was found when cells (85% of the total) were arrested in G1 by growing them to confluence (FIG. 1A). In addition to γ-irradiation, other DNA-damaging agents, such as adriamycin, were found to similarly induce σ expression in HCT116 cells (FIG. 1B). The induction of σ by DNA damage was not confined to HCT116 cells, as several other colorectal cancer cell lines were shown to express σ at relatively high levels following adriamycin treatment (FIG. 1B). Previous reports have shown that σ expression is limited to epithelial cells. In agreement with these observations, we found that σ was not detectably expressed in either exponentially growing or γ-irradiated human diploid fibroblasts or in human endothelial cells (data not shown).

Of seven CRC cell lines analyzed, the four that expressed higher levels of σ following DNA damage contained endogeous wild-type p53 alleles, while the three in which σ was uninduced contained mutant p53 genes (FIG. 1B). This observation was consistent with the hypothesis that p53 was responsible for the DNA damage-induced expression of σ.

To test more directly the ability of p53 to modulate σ expression, we infected CRC cells with a replication defective adenovirus engineered to express wild-type p53. Exogenous p53 expression induced a pronounced rise in σ RNA which was first observed at 3 hours following infection, earlier than p21 or any other genes known to be induced by p53 in these cells (FIG. 2A and data not shown). The maximum induction (18-fold) of σ was achieved at ~12 hr after infection. The induction of σ by exogenous p53 (compared to a control adenovirus, Ad-β, encoding β-galactosidase) was consistently observed in each of seven CRC lines tested (examples in FIG. 2B). Additionally, σ was induced by p53 in a CRC line with a deletion of p21, demonstrating that the induction of a was not secondary to an induction of a p21-mediated growth arrest stimulated by p53 (FIG. 2B).

Northern Blot Analysis

Total RNA was prepared by CsCl gradient ultracentrifugation of guanidine isothiocyanate-lysed cells as described. A 375 bp probe specific for the 3' untranslated region of σ was generated by PCR using EST W79136 as template and the primers 5'-ACAGGGGAACTTT ATTGAGAGG-3' (SEQ ID NO: 7) and 5'-AAGGGCTCCGTGGAGAGGG-3' (SEQ ID NO: 8). Probes for p21 were generated by a restriction endonuclease digestion of pCEP-WAF1 (El-Deiry et al., 1993) with Sal I and isolation of the 2.1 kb cDNA fragment. The probe for the constitutively expressed gene EF1 was obtained by RT-PCR with the primers 5'-GAAAACTACCCCTAAAAGCC-3' (SEQ ID NO: 9) and 5'-GTTGGGTGGCAGGTAT TAGG-3' (SEQ ID NO: 10). Hybridizations were performed in QuickHyb using the manufacturer's instructions (Stratagene).

EXAMPLE 3

This example demonstrates the basis for the p53 dependence of σ induction.

To determine the molecular basis for the p53 induction of σ, a genomic clone containing the human σ gene and ~100 kb of surrounding sequences was obtained by screening a bacterial artificial chromosome (13AC) library. Fluorescence in situ hybridization (FISH) analysis of metaphase chromosomes with a probe generated from this BAC clone localized a to chromosome band 1p35 (FIG. 3A). Sequencing of relevant regions of the BAC revealed a presumptive transcription start site (TSS) when assessed with the Neural Network Promoter Prediction program; the TSS coincided with the 5' end of the most complete σ cDNA clone.

To test the ability of sequences within the σ promoter to mediate p53-dependent transcription, subclones from the BAC, containing 1 kb or 4 kb of sequences upstream of TSS, were placed upstream of a promoterless luciferase reporter gene (FIG. 3A). The reporter containing 4 kb of promoter sequences was efficiently activated by wt (but not mutant) p53, while the reporter with 1 kb had no p53-dependent activity (data not shown). This localized the presumptive p53-regulatory region to the region between 1 to 4 kb from the TSS. A 9.5 kb BamH 1 fragment containing the entire σ coding region plus 8.5 kb of upstream sequences was then subcloned and completely sequenced (deposited at GenBank). This region of the BAC revealed a presumptive transcription start site (TSS) when assessed with the Neural Network Promoter Prediction program (http://dot.imgen.bcm.tmc.edu:9331/seq-search/gene-search.html); the TSS coincided with the 5' end of the most complete σ cDNA clone. The sequence revealed two potential p53-binding sites, named BDS-1 and BDS-2, located 2.5 and 1.8 kb upstream of the TSS, respectively, and within the region of the promoter predicted to contain functionally active p53 response elements in the transfection experiments (FIG. 3A). Restriction fragments containing each of these two sites were then individually cloned upstream of a luciferase reporter containing a minimal promoter. A Pst I-Hind III fragment containing BDS-2, but not a similarly-sized fragment containing BDS-1, was found to have substantial p53-dependent activity in this assay (FIG. 3B). To prove that the BDS-2 sequence within the Pst I-Hind III fragment was indeed responsible for p53-dependent activation, a 37 bp sequence containing the 20 bp BDS-2 was multimerized and cloned upstream of a minimal promoter and luciferase reporter. The BDS-2 sequences endowed the reporter with exceptional p53-dependent activation properties. Two to three copies of BDS-2 provided substantially more activation than 13 copies of the p53-binding consensus sequences present in the standard p53 reporter $PG_{13}$-luc (FIG. 3C). Mutant p53 had no activating effect, and nucleotide substitutions at residues of BDS-2 predicted to be critical for p53 binding completely abrogated p53-dependent activity (FIG. 3C).

σ Genomic Clones and Reporter Constructs

A BAC library (Research Genetics) was screened with PCR, using the primers

5'-GTGTGTCCCCAGAGCCATGG-3' (SEQ ID NO: 11) and 5'-ACCTTCTCCCGGTACTCACG-3' (SEQ ID NO: 12), yielding a 278 bp product from the 5' end of the a cDNA. A BAC containing σ was digested with BamH I and a 9.5 kb fragment including the complete coding sequence of σ was subcloned into pBR322. The resulting construct was used for subcloning smaller fragments, which were placed into a vector containing the luciferase reporter gene and a minimal promoter derived from the adenovirus E1B gene. To test the activity of presumptive p53-binding sites, the following oligonucleotide pairs were used: 5'-CCTGTAGCATTAGCCCAGACATGTCCCTACTC-CGTAC-3' (SEQ ID NO:13) and 5'-GGAGTAGGGACA-TGTCTGGGCTAATGCTACAGGGTAC-3' (SEQ ID NO: 14) for BDS-2 and 5'-CCTGTAGAATTATCCCAGAAA-TTTCCCT ACTCCGTAC-3' (SEQ ID NO:15) and 5'-GGAGTAGGGAAATTTCTGGGATAATTCTACAGG-GTAC-3' (SEQ ID NO: 16) for BDS-2*, altered at critical p53-binding residues. The oligonucleotide pairs were concatemerized and subcloned into the Kpn I site of pGL3-basic, containing a minimal promoter derived from the E1B gene and the luciferase reporter (Promega). Transfections were performed in SW480 cells using Lipofectamine (Life Sciences), using 1 ug of reporter plasmid, and 2 ug of either pCEP4 (Invitrogen) or 2 ug pCEP4 encoding wt p53 or mutant p53 R175H. A β-galactosidase reporter construct (0.5 ug) was included in each transfection to control for efficiency. Luciferase and β-galactosidase activities were assessed 24 h following transfection using reagents from Promega and ICN Pharmaceuticals, respectively.

FISH

P1 probes specific for chromosomes 2p (red) and 11q25 (green) were labeled with digoxigenin-11-dUTP and biotin-16-dUTP, respectively, by nick translation. Cells were fixed on slides and pretreated with RNase and pepsin. Multicolor FISH on interphase cells was performed following standard procedures. Digoxigenin-labeled probes were detected with an anti-digoxin mouse monoclonal, TRITC-conjugated-rabbit-anti-mouse and TRITC-conjugated goat-anti-rabbit antibodies, whereas biotinylated probes were detected with FITC Avidin-DCS (Vector). Cells were counterstained with DAPI.

For chromosomal mapping of the s gene, a BAC containing the σ gene was labeled with biotin-16-dUTP. Human prometaphase spreads were fixed on slides and pretreated with RNase and pepsin. Hybridized probe sequences were detected as described above, and chromosomes were counterstained with DAPI. The resulting banding pattern and the hybridization signals we re evaluated by standard epifluorescence microscopy (Nikon Eclipse E800). A total of 50 randomly seleted prometaphases were evaluated. All of them showed hybridization signals on the distal arm of both chromatids of the homologous chromosomal regions 1p35. In addition, fractional length measurements were performed as described, confir ming the mapping of s to the 1p35 band. Photographs were taken using a CCD camera (Photometrics). The sequentially recorded gray-scale images w ere pseudocolored and merged using the softiware program IPLab (Signal Analytics Cooperation, Vienna, VI).

EXAMPLE 4

This example demonstrates that σ expression disrupts G2/M progression.

cDNA clones of σ were obtained from EST depositories. The sequences of the cDNA clones revealed important corrections to previously published sequences, which were verified by the sequence of genomic clones (new cDNA sequence deposited at GenBank). To determine whether the expression of σ was causally related to the G2 arrest associated with its induction, we tagged the cDNA with a hemagglutinin (HA) epitope and cloned it into an adenoviral vector to create Ad-σ. HCT116 cells underwent remarkable morphological changes following infection with Ad-σ, and by 30 hours were flattened and enlarged, resembling cells treated with γ-irradiation. Staining of Ad-σ infected cells with an anti-HA antibody showed it to be cytoplasmic, and in some cells a striking perinuclear localization of the σ protein was evident (FIG. 4A). DAPI staining demonstrated a nuclear enlargement that accompanied the size increase in cells expressing σ (FIG. 4A).

Figure 4B:
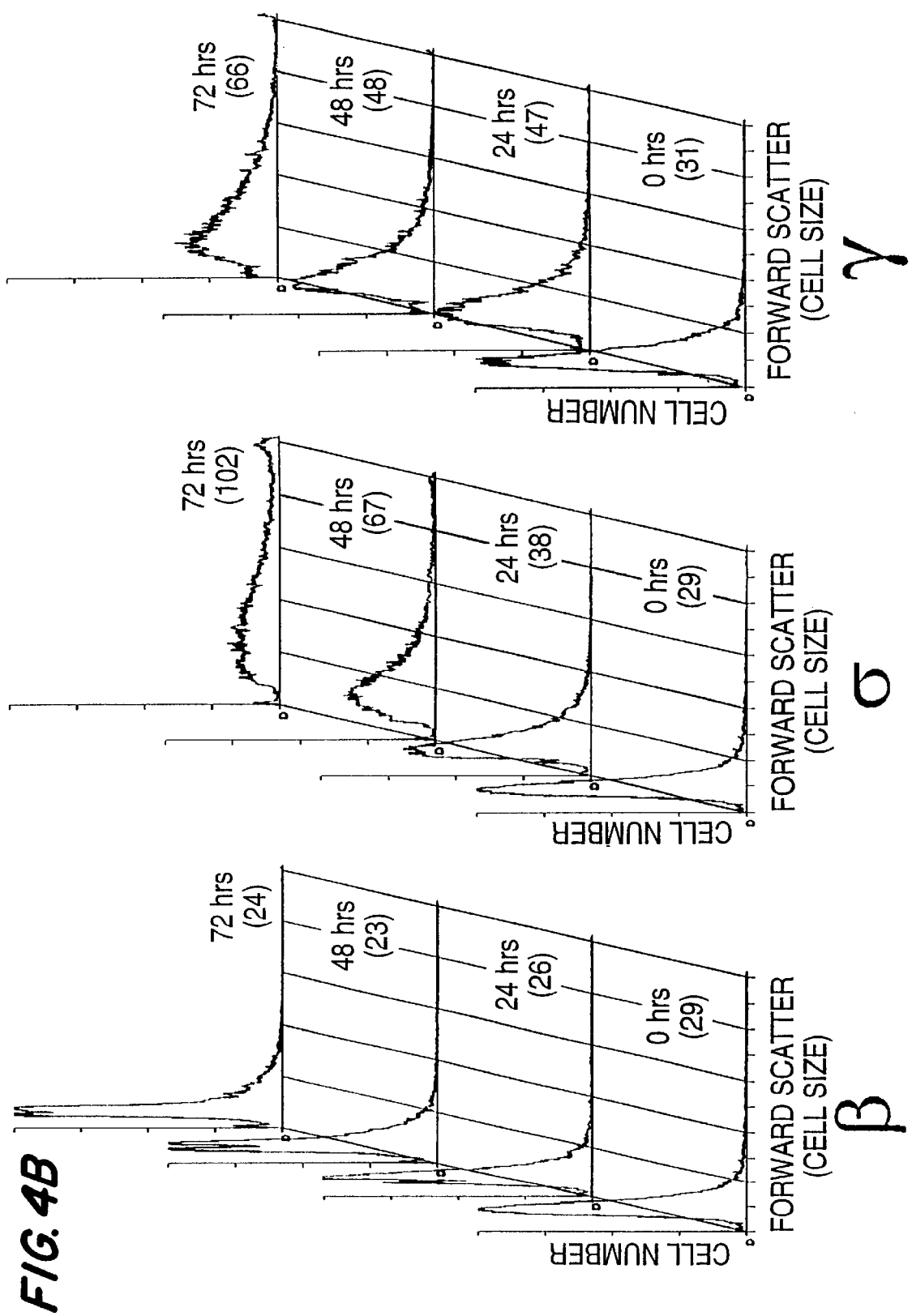

Flow cytometry allowed us to confirm and quantitate the increase in size ofHCT116 cells expressing σ (FIG. 4B). A similar size increase occurred in γ-irradiated cells (FIG. 4B). Flow cytometry additionally revealed a G2/M arrest (DNA content of 4N) in cells infected with Ad-σ compared to those infected with the control Ad-β (24 hr time point in FIG. 5A, B). There was no evidence of chromosome condensation or nuclear membrane dissolution in these cells, even after treatment with the microtubule disrupting agents nocodazole or colcemid to stabilize any mitoses that may have occurred. There was a complete block of cellular proliferation after Ad-σ infection, with no increase in cell number observed over 7 days. Infection of four other CRC cell lines, as well as normal prostate epithelial cells, resulted in a similar arrest of the cell cycle, with a build-up of cells containing a DNA content of 4N and no evidence of mitosis (data not shown).

Recombinant Adenovirus Generation

The σ containing EST W79136 was used as template for PCR, employing the primers 5'-GCATGCGGTACCTAA-TACGACTCACTATAGGGCGACCACCATGGAGAGA-GCCAGTCTG AT-3' (SEQ ID NO: 17) and 5'-ACCTCCGGATCCTTAGCTAGCGTAAT CTGGAA-CATCGTAAGC GTAATCTGGAACAT CGTATCCAC-CGCTCTGGGGC TCCTGGGGAG-3' (SEQ ID NO: 18). The 849 bp product was inserted into the Kpn I and EcoRV sites of pHRCMV, an adenoviral shuttle vector in which the expression of inserted genes is driven by a CMV promoter. Recombinant Ad-σ and Ad-β adenoviruses were generated in 911 cells. Viruses were purified via a CsCl gradient and titers determined by plaque assays. Cells were infected with adenoviruses at an MOI of ~100:1.

Immunohistochemistry

Cells were fixed in Histochoice (Amresco), permeabilized with 1% NP40 in phosphate buffered saline (PBS), and blocked in goat serum for 1 h. The 3F10 rat monoclonal anti-HA antibody (Boehringer Mannheim) was applied in GT (goat serum containing 0.05% Tween 20). After washing in PBST (PBS with 0.05% Tween 20), a biotin-labeled goat anti-rat Ig antibody (Pierce) was diluted in GT and applied for 30 min. After 3 washes in PBST for 5 min. each, streptavidin-fluorescein (Molecular Probes), diluted in PBST, was used for detection. Cells were counterstained with 4,6-diamidino-2-phenylindole (DAPI). Slides were mounted in DAPCO/glycerin and analyzed with a Nikon Eclipse E800 microscope equipped with a CCD camera (Photometrics). Images were pseudocolored using the software program IPLab (Signal Analytics Cooperation, Vienna, VI).

Flow Cytometry

Cells were rinsed in Hanks' Balanced Salt Solution (HBSS), trypsinized, collected by centrifugation, and resuspended in 40 ul HBSS. Ten volumes of PBS containing 4% formaldehyde, 1% NP40 and 4 ug/ml Hoechst H33528 were added and flow cytometry performed with a EPICS 752 instrument (Coulter, Hialeah, Fla.), excluding cell doublets.

EXAMPLE 5

This example demonstrates that σ expression can induce an uncoordinated growth arrest.

At 24 hours following Ad-σ infection of HCT116 cells, the cell cycle profiles were very similar to those observed in γ-irradiated cells (FIG. 5B, FIG. 5C). However, a significant difference became apparent at longer times after infection. While irradiated cells remained in a G2-arrested state, with a nuclear DNA content of 4N, many σ-expressing cells entered into a DNA synthetic phase, resulting in a significant population of cells with a DNA content greater than 4N at 48 and 72 hours (FIG. 5B, FIG. 5C). Addition of colcemid 30 hr after Ad-σ infection did not prevent this polyploidization (data not shown). This increased ploidy was further demonstrated to result from true DNA reduplication by interphase FISH analysis. Two different chromosomal loci were assessed 72 hours following infection with either Ad-σ or Ad-β. For each analyzed chromosomal locus, nearly half of the σ-expressing cells contained more than the four hybridization signals per locus expected in G2 (one signal from each chromatid; FIG. 6A, right panel). Thirty percent of the cells contained 8 signals, 11% contained 16 signals, and 1% contained 32 signals, representing cells with DNA contents of 8N, 16N, and 32N, respectively (FIG. 6B). The signals in polyploid cells were nearly always paired, representing bivalent chromosomes (115 of 125 cells examined). However, each pair was separated from other pairs in the same nucleus (FIG. 6A, right). This clearly indicated that chromatids had detached from each other prior to a new round of DNA replication and creation of new bivalents. Very few cells infected with Ad-σ exhibited more than four hybridization signals/probe, and many exhibited two signals (representing cells in G1; FIG. 6A, left panel and FIG. 6B).

These results suggested that exogenous σ expression can produce an uncoordinated block in which cycles of DNA synthesis can proceed without intervening mitoses. One potential reason for this uncoordinated arrest, compared to the coordinated arrest observed in γ-irradiated cells, involves p21. Irradiated cells express both σ and p21 in a p53-dependent manner, and p21 can prevent DNA synthesis through its inhibition of cyclin-dependent kinases. However, if σ expression alone is generated by infection with Ad-σ, no concomitant increase in cdk inhibitor expression would be expected and the cells, though unable to undergo a normal mitosis, may still be able to re-enter S phase. This explanation predicts that in p21-deficient cells, a similar uncoordinated arrest, with chromosome duplication in the absence of mitosis, would occur after γ-irradiation. Previous experiments were consistent with this prediction and confirmed by the experiments shown in FIG. 5D. Forty-eight hours after γ-irradiation of p21-deficient HCT116 cells, a marked increase in cells with 8N chromosome complements was observed, resulting in a cell cycle profile similar to that observed in cells infected with Ad-σ.

To further explore the nature of the block and subsequent polyploidization produced by σ-expressing cells, cells were observed with time-lapse microscopy. Of 24 σ-expressing cells observed continuously for three days, none underwent a normal cell division such as that consistently observed in β-galactosidase-expressing cells (FIG. 7). Forty-eight percent of the cells rounded up as if they were beginning mitosis and then initiated cytokinesis, yielding two connected daughter cells which never completely separated. These incompletely divided cells subsequently re-fused, forming one large cell with a single nucleus (FIG. 7, top row). The remainder of the cells (52%) rounded, never divided, and finally died through an apoptotic event (accompanied by cytoplasmic blebbing and nuclear degradation). p21-deficient HCT116 cells (but not parental HCT116 cells) exhibited similar aberrant cytokinetic events following γ-irradiation, with 19 of 20 cells examined in detail entering into an abortive cytokinesis morphologically identical to that shown in FIG. 7.

Time-lapse Video Microscopy

Tissue culture flasks were sealed under 5% $CO_2$ and kept at 37° C. on a Fryer Temperature Controller A-50 equipped Nikon inverted microscope. Video recordings were taken using a CCD camera (Optronics DEI-470) and a time lapse video recorder (Hitachi VT-L2000 AR) recording one frame every 17 seconds.

REFERENCES

Agarwal, M. L., Agarwal, A., Taylor, W. R., and Stark, G. R. (1995). p53 controls both the G2/M and the G1 cell cycle checkpoints and mediates reversible growth arrest in human fibroblasts. Proc. Natl. Acad. Sci. USA 92, 8493–8497.

Aitken, A. (1995). 14-3-3 proteins on the MAP. Trends Biochem. Sci. 20, 95–97.

Aloni-Grinstein, R., Schwartz, D., and Rotter, V. (1995). Accumulation of wild-type p53 protein upon gamma-irradiation induces a G2 arrest-dependent immunoglobulin kappa light chain gene expression. EMBO J. 14, 1392–1401.

Blomstrom, D. C., Fahey, D., Kutny, R., Korant, B. D., and Knight, E. J. (1986). Molecular characterization of the interferon-induced 15-kDa protein: Molecular cloning and nucleotide and amino acid sequence. J. Biol. Chem. 261, 8811–8816.

Brugarolas, J., Chandrasekaran, C., Gordon, J. I., Beach, D., Jacks, T., and Hannon, G. J. (1995). Radiation induced cell cycle arrest compromised by p21 deficiency. Nature 377, 552–557.

Conklin, D. S., Galaktionov, K., and Beach, D. (1995). 14-3-3 proteins associate with cdc25 phosphatases. Proc. Natl. Acad. Sci. USA 92, 7892–7896.

Cos, L. S., and Lane, D. P. (1995). Tumour suppressors, kinases and clamps: how p53 regulates the cell cycle in response to DNA damage. Bioessays 17, 501–508.

Davis, L. G., Dibner, M. D., and Battery, J. F. (1986), Basic Methods in Molecular Biology (New York: Elsevier Science Publishing).

Deng, C., Zhang P., Harper, J. W., Elledge, S. J., and Leder, P. (1995). Mice lacking p21/Cip/WAF1 undergo normal development, but are defective in G1 checkpoint control. Cell 82, 675–684.

El-Deiry, W. S., Kern, S. E., Pietenpol, J. A., Kinzler, K. W., and Vogelstein, B. (1992). Definition of a consensus binding site for p53. Nature Genetics 1, 45–49.

El-Deiry, W. S., Tokino, T., Velculescu, V. E., Levy, D. B., Parsons, R., Trent, J. M., Lin, D., Mercer, W. E., Kinzler, K. W., and Vogelstin, B. (1993). WAF1, a potential mediator of p53 tumor suppression. Cell 75, 817–825.

Fallaux, F. J., Kranenburg, O., Cramer, S. J., Houweling, A., Van Ormondt, H., Hoeben, R. C., and Van Der Eb, A. J. (1991). Characterization of 911: a new helper cell line for the titration and propagation of early region 1-deleted adenoviral vectors. Hum. Gene Ther. 7, 215–222.

Ford, J. C., al-Khodairy, F., Fotou, E., Sheldrick, K. S., Griffiths, D. J., and Carr, A. M. (1994). 14-3-3 protein homologs required for the DNA damage checkpoint in fission yeast. Science 265, 533–535.

Fu, H., Xia, K. Pallas, D. C., Cui, C., Conroy, K., Narsimhan, R. P., Mamon, H., Collier, R. J., and Robert, T. M. (1994). Interaction of the protein kinase Raf-1 with 14-3-3 proteins. Science 266.

Goi, K., Takagi, M., Iwata, S., Delia, D., Asada, M., Donghi, R., Tsunematsu, Y., Nakazawa, S., Yamamoto, H., Yokota, J., Tamura, K., Saeki, Y., Utsunomiya, J., Takahashi, T., Ueda, R., Ishioka, C., Eguchi, M., Kamata, N., and Mizutani, S. (1997). DNA damage-associate dysregulation of the cell cycle and apoptosis control in cells with germ-line p53 mutation. Cancer Res. 57, 1895–1902.

Harper, J. W., Adami, G. R., Wei, N., Keyomarsi, K., and Elledge, S. J. (1993). The p21 Cdk-interacting protein Cip 1 is a potent inhibitor of G1 cyclin-dependent kinases. Cell 75, 805–816.

Hartwell, L. H., and Kastan, M. B. (1994). Cell cycle control and cancer. Science 266, 1821–1828.

Honda, R., Ohba, Y., and Yasuda, H. (1997). 14-3-3 zeta protein binds to the carboxyl half of mouse weel kinase. Biochem. Biophys. Res. Commun. 230, 262–265.

Kern, S. E., Pietenpol, J. A., Thiagalingam, S., Seymour, A., Kinzler, K. W., and Vogelstein, B. (1992). Oncogenic forms of p53 inhibit p53-regulated gene expression. Science 256, 827–30.

Leffers, H., Madsen, P., Rasmussen, H. H., Honore, B., Andersen, A. H., Walbum, E., Vandekerckhove, J., and Celis, J. E. (1993). Molecular cloning and expression of the transformation sensitive epithelial marker stratifin. A member of a protein family that has been involved in the protein kinase C signaling pathway. J. Mol. Biol. 231, 982–998.

Levine, A. J. (1997). p53, the cellular gatekeeper for growth and division. Cell 88, 323–331.

Lichter, P., Tang, C. J., Call, K., Hermanson, G., Evans, G. A., Housman, D., Ward, D. C. (1990). High-resolution mapping of human chromosome 11 by in situ hybridization with cosmid clones. Science 247, 64–69.

Lichter, P., and Cremer, T. (1992). In Human Cytogenetics: A Practical Approach (eds. Rooney, D. E. and Czepulkowski, B. H.) 1570192 (IRL, Oxford, 1992).

Morgan, S. E., and Kastan, M. B. (1997. p53 and ATM: cell cycle, cell death, and cancer. Adv. Cancer Res. 71, 1–25.

Paulovich, A. G., Toczyski, D. P., and Hartwell, L. H. (1997). When checkpoints fail. Cell 88, 315–321.

Polyak, K. Yong, X., Zweier, J. L., Kinzler, K. W., and Vogelstein, B. (1997) A model for p53-induced apoptosis, Nature, in press.

Polyak, K., Waldman, T., He, T. -C., Kinzler, K. W., and Vogelstein, B. (1996). Genetic determinants of p53 induced apoptosis and growth arrest. Genes & Development 10, 1945–1952.

Prasad, G. L., Valverius, E. M., McDuffie, E., and Cooper, H. L. (1992). Complementary DNA cloning of a novel epithelial cell marker protein, HME 1, that may be down-regulated in neoplastic mammary cells. Cell Growth. Differ. 3, 507–513.

Reuther, G. W., Fu, H., Cripe, L. D., Collier, R. J., and Pendergast, A. M. (1994). Association of the protein kinase c-Bcr and Bcr-Abl with proteins of the 14-3-3 family. Science 266, 129–133.

Sladeczek, F., Camonis, J. H., Burnol, A. F., and Le Bouffant, F. (1997). The Cdk-like protein PCTAIRE-1 from mouse brain associates with p11 and 14-3-3 proteins. Mol. Gen. Genet. 254, 571–577.

Stewart, N., Hicks, G. G., Paraskevas, F., and Mowat, M. (1995). Evidence for a second cell cycle block at G2/M by p53. Oncogene 10, 109–115.

Velculescu, V. E., Zhang, L. Vogelstein, B., and Kinzler, K. W. (1995). Serial analysis of gene expression. Science 270, 484–487.

Velculescu, V. E., Zhang, L., Zhou, W., Vogelstein, J., Basrai, M. A., Bassett, D. E., Hieter, P., Vogelstein, B., and Kinzler, K. W. (1997). Characterization of the yeast transcriptome. Cell 88.

Waldman, T., Kinzler, K. W., and Vogelstein, B. (1995). p21 is Necessary for the p53-Mediated G1 Arrest in Human Cancer Cells. Cancer Res. 55, 5187–5190.

Waldman, T., Lengauer, C., Kinzler, K. W., and Vogelstein, B. (1996). Uncoupling of S phase and mitosis induced by anticancer agents in cells lacking p21. Nature 381, 713–716.

Wang, W., and Shakes, D. C. (1996). Molecular evolution of the 14-3-3 protein family. J. Mol. Eval. 43, 384–398.

Weinert, T. A., Kiser, G. L., and Hartwell, L. H. (1994). Mitotic checkpoint genes in budding yeast and the dependence of mitosis of DNA replication and repair. Genes & Development 8, 652–665.

Xiong, Y., Hannon, G. J., Zhang, H., Casso, D., Kobayashi, R., and D., B. (1993). p21 is a universal inhibitor of cycline kinases. Nature 366, 701–704.

What is claimed is:

1. A method for screening potential therapeutic agents for the ability to suppress the growth of tumor cells by activating the expression of 14-3-3σ, comprising the steps of:
   incubating a potential therapeutic agent with a cell which contains a 14-3-3σ reporter construct, said reporter construct comprising a 14-3-3σ transcription regulatory region covalently linked in a cis configuration to a gene encoding an assayable product;
   measuring the production of the assayable product, a potential therapeutic agent which increases the production by the cell of the assayable product being an agent which will suppress the growth of tumor cells by activating the expression of 14-3-3σ.

2. The method of claim 1 wherein the 14-3-3σ transcription regulatory region comprises about 1.815 kb upstream from 14-3-3σ transcriptional start site.

3. The method of claim 1 wherein the 14-3-3σ transcription regulatory region comprises the sequence of SEQ ID NO: 5.

4. A method for screening test compounds to identify those which are potential anti-tumor agents, comprising the steps of:
   determining DNA content of 14-3-3σ gene-defective human cells incubated in the presence and in the absence of a test compound, wherein a test compound which causes DNA accumulation in the 14-3-3σ gene-defective human cells is identified as a potential anti-tumor agent.

5. The method of claim 4 wherein the DNA accumulation is in excess of four times the cells' haploid DNA content.

6. The method of claim 4 wherein the DNA content of the cells is determined by staining the cells with a DNA-binding dye.

7. The method of claim 4 wherein the DNA content of the cells is determined by fluorescence in situ hybridization (FISH).

8. The method of claim 4 wherein the 14-3-3 σ gene-defective human cells are colonic cells.

9. The method of claim 4 further comprising the steps of:

determining DNA content of 14-3-3σ gene-normal human cells incubated in the presence and in the absence of the potential anti-tumor agent;

identifying a potential anti-tumor agent which preferentially causes DNA accumulation in the 14-3-3σ gene-defective human cells as compared to the 14-3-3σ gene-normal human cells.

10. The method of claim 6 wherein the DNA-binding dye is selected from the group consisting of H33258 and propidium iodide.

11. The method of claim 6 further comprising measuring the incorporation of the DNA-binding dye by flow cytometry.

12. A method of screening for potential anti-tumor agents, comprising the steps of:

determining viability of 14-3-3σ gene-defective human cells incubated in the presence and in the absence of a test compound;

selecting a test compound which causes cell death in the 14-3-3σ gene-defective cells as a potential anti-tumor agent.

13. The method of claim 12 wherein the viability of the cells is determined by applying a dye to the cell, incorporation of the dye by the cell indicating death of the cell.

14. The method of claim 12 wherein the 14-3-3σ gene-defective human cells are colonic cells.

15. The method of claim 13 wherein the dye is trypan blue.

16. A method of screening for potential anti-tumor agents, comprising the steps of:

determining apoptosis of 14-3-3σ gene-defective human cells incubated in the presence and in the absence of a test compound;

selecting a test compound which causes apoptosis in the 14-3-3σ gene-defective human cells as a potential anti-tumor agent.

17. The method of claim 16 wherein the apoptosis of the cells is determined by staining the cells with a DNA-binding dye and observing chromosomes of the cells, condensation of the chromosomes indicating apoptosis of the cells.

18. The method of claim 16 wherein the apoptosis of the cells is determined by subjecting DNA of the cells to gel electrophoresis, wherein observation of a DNA ladder indicates apoptosis of the cells.

19. The method of claim 16 wherein the apoptosis of the cells is determined by detecting abnormal breaks in DNA of the cells, wherein abnormal breaks in the DNA indicate apoptosis of the cells.

20. The method of claim 16 wherein the 14-3-3σ gene-defective human cells are colonic cells.

21. The method of claim 16 further comprising the steps of:

determining viability of 14-3-3σ gene-normal human cells incubated in the presence and in the absence of the selected test compound;

identifying a selected test compound which preferentially causes cell death in the 14-3-3σ gene-defective human cells as compared to the 14-3-3σ gene-normal human cells.

22. The method of claim 17 wherein the DNA-binding dye is H33258.

23. The method of claim 19 wherein the abnormal breaks in the DNA are detected by a terminal DNA transferase assay.

24. The method of claim 19 wherein the abnormal breaks in the DNA are detected by a nick translation assay.

25. A homozygous 14-3-3σ gene-defective human cell line.

26. The homozygous 14-3-3σ gene-defective human cell line of claim 25 which comprises colonic cells.

27. A pair of isogenic cell lines wherein the first cell line of the pair is a homozygous 14-3-3σ gene-defective human cell line and the second cell line of the pair is a homozygous 14-3-3σ gene-normal human cell line.

* * * * *

UNITED STATES PATENT AND TRADEMARK OFFICE
CERTIFICATE OF CORRECTION

PATENT NO.    : 6,335,156 B1
DATED         : January 1, 2002
INVENTOR(S)   : Heiko Hermeking et al.

It is certified that error appears in the above-identified patent and that said Letters Patent is hereby corrected as shown below:

Column 39,
Line 57, "the" has been deleted in the phrase "the production".

Column 41,
Line 14, "the" has been deleted in the phrase "the incorporation".

Signed and Sealed this

Twenty-sixth Day of November, 2002

Attest:

JAMES E. ROGAN
Director of the United States Patent and Trademark Office

Attesting Officer